(12) United States Patent
Aoki et al.

(10) Patent No.: US 7,842,726 B2
(45) Date of Patent: Nov. 30, 2010

(54) CARNITINE DERIVATIVE, SALT THEREOF, EXTERNAL SKIN PREPARATION AND COSMETIC MATERIAL

(75) Inventors: Hirobumi Aoki, Chiba (JP); Harumi Kamachi, Chiba (JP); Yohei Kurata, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 281 days.

(21) Appl. No.: 12/088,792

(22) PCT Filed: Sep. 21, 2006

(86) PCT No.: PCT/JP2006/319221

§ 371 (c)(1),
(2), (4) Date: Mar. 31, 2008

(87) PCT Pub. No.: WO2007/043339

PCT Pub. Date: Apr. 19, 2007

(65) Prior Publication Data

US 2009/0234153 A1 Sep. 17, 2009

Related U.S. Application Data

(60) Provisional application No. 60/724,276, filed on Oct. 7, 2005, provisional application No. 60/777,551, filed on Mar. 1, 2006.

(30) Foreign Application Priority Data

Sep. 30, 2005 (JP) ............... 2005-288462
Feb. 22, 2006 (JP) ............... 2006-045167

(51) Int. Cl.
*A61K 31/225* (2006.01)
*C07C 229/00* (2006.01)

(52) U.S. Cl. .............. 514/547; 554/108; 554/52; 560/155

(58) Field of Classification Search ........... 554/36, 554/108; 514/547; 560/1, 65, 155
See application file for complete search history.

(56) References Cited

U.S. PATENT DOCUMENTS 4,401,827 A * 8/1983 de Witt ............... 560/1
5,043,355 A * 8/1991 Cavazza ............. 514/547

(Continued)

FOREIGN PATENT DOCUMENTS

DE 3726945 A1 2/1989

(Continued)

OTHER PUBLICATIONS

Berge et al., Pharmaceutical Salts, 1977, Journal of Pharmaceutical Sciences, vol. 66, No. 1, pp. 1-19.*

(Continued)

*Primary Examiner*—Daniel M Sullivan
*Assistant Examiner*—Yate' K Cutliff
(74) *Attorney, Agent, or Firm*—Sughrue Mion, PLLC

(57) ABSTRACT

To provide novel carnitine derivatives and salts thereof that are resistant to hydrolysis in the presence of aqueous media, and also provide external skin preparations and cosmetics that are excellent in storage stability, product life, skin affinity and percutaneous absorption properties. In particular, to provide novel α-branched acyl carnitine derivatives and salts thereof, external skin preparations and cosmetics comprising specific α-branched acyl carnitine derivatives and/or salts thereof.

21 Claims, 2 Drawing Sheets

U.S. PATENT DOCUMENTS

2004/0166127 A1* 8/2004 Haadem .................. 424/401
2004/0176448 A1* 9/2004 Blatt et al. .................. 514/547

FOREIGN PATENT DOCUMENTS

| FR | 2694195 A1 | 2/1994 |
|----|------------|--------|
| GB | 2028826 A | 3/1980 |
| JP | 7-309711 A | 11/1995 |
| JP | 2000-16916 A | 1/2000 |
| JP | 2001-64147 A | 3/2001 |
| JP | 2002187821 A | 7/2002 |
| JP | 3434995 B2 | 5/2003 |
| WO | 9844918 A1 | 10/1998 |
| WO | 0004870 A2 | 2/2000 |
| WO | 2005115326 A1 | 12/2005 |

OTHER PUBLICATIONS

Taizo et al, Hair cosmetics, 2002, JP2002-187821, English Translation, ten (10) pages.*

Shcaffer et al., Morphological behaviour of mixed skin lipids, 1999, Molecular crystals and liquid crystals Science and Technology, Section A, vol. 329, pp [791]/179 - [798]/186.*

Database Registry [Online] Chemical Abstracts Service, Columbus, Ohio, US; Dec. 15, 2005, XP002418834 retrieved from STN, RN 870003-37-5.

Database Registry [Online] Chemical Abstracts Service, Columbus, Ohio, US; Dec. 15, 2005, XP002418835 retrieved from STN, RN 870003-40-0.

Database Registry [Online] Chemical Abstracts Service, Columbus, Ohio, US; Dec. 15, 2005, XP002418836 retrieved from STN, RN 870003-39-7.

Nakanishi, Toyofumi et al., "Synthesis of acylcarnitines for differential diagnosis of metabolic disorders", Database Registry [Online] Chemical Abstracts Service, Columbus, Ohio, US; 1993, XP002418837, retrieved from STN, Database accession No. 1994:245706 abstract.

* cited by examiner

CARNITINE DERIVATIVE, SALT THEREOF, EXTERNAL SKIN PREPARATION AND COSMETIC MATERIAL

REFERENCE TO RELATED APPLICATIONS

This application is an application filed under 35 U.S.C. §111(a) claiming benefit pursuant to 35 U.S.C. §119(e) of the filing dates of Provisional Applications No. 60/724,276 filed Oct. 7, 2005 and No. 60/777,551 filed Mar. 1, 2006, pursuant to 35 U.S.C. §111(b).

FIELD OF THE INVENTION

The present invention relates to external skin preparations and cosmetics. More particularly, the invention relates to external skin preparations and cosmetics that contain carnitine derivatives and/or salts thereof and stimulate lipid metabolism. The invention is also concerned with novel carnitine derivatives and salts thereof.

BACKGROUND OF THE INVENTION

Carnitine is known to play an important role in human lipid metabolism. In cells, the carnitine is enzymatically bound to the fatty acids from fats and transports the fatty acids into the mitochondria, an organelle where fat is burned. Accordingly, the carnitine has a function as a carrier for the fatty acids and is essential to the lipid metabolism. The fatty acids are β-oxidized in the mitochondria and are converted into energy in the form of ATP in living body.

The lipids are important not only as an energy source but also as constituents of the human body. All cell membranes are composed of the lipids. On a macro scale, the lipids control evaporation of moisture from the body in the form of sebum and intercellular lipids.

Excessive lipids lead to obesity as a result of the accumulation of subcutaneous fat, and cause many cosmetic and QOL (quality of life) problems, including cellulite formation, shiny and greasy skin due to excessive sebum, seborrheic dermatitis and consequent hair loss, acnes, body odor, and skin aging due to decreased lipid metabolism.

As described above, the lipid metabolism requires that the fatty acids be transported into the mitochondria, for which the carnitine is responsible. Accordingly, the lipid metabolic rate is dependent on the amount of carnitine in the cells. Increasing the carnitine concentration in target tissues will stimulate the lipid metabolism and will prevent and eliminate excessive lipids and associated problems.

For such reasons, percutaneous absorption of various external skin preparations containing carnitine has been studied and proposed to stimulate the lipid metabolism (Patent Documents 1 to 4). However, such external skin preparations, which contain L-carnitine and salts thereof, have been unable to achieve satisfactory effects. The reason is probably that because the L-carnitine and salts thereof are hydrated quite easily, their direct use results in poor skin affinity and percutaneous absorption properties, and enough carnitine hardly reaches the tissue in which the lipid metabolism is to be performed.

Slimming external skin preparations are proposed, which contain a straight-chain acyl carnitine (in which the carnitine is modified with a straight-chain fatty acid residue) capable of higher dermatological effects than carnitine itself. As an example, a slimming external skin preparation contains palmitoyl-L-carnitine (L-carnitine palmitate), carnitine, caffeine and coenzyme A (Patent Document 5).

[Patent Document 1] Japanese Patent No. 3434995
[Patent Document 2] JP-A-H07-309711
[Patent Document 3] JP-A-2000-16916
[Patent Document 4] JP-A-2001-64147
[Patent Document 5] French Patent No. 2694195

DISCLOSURE OF THE INVENTION

Problems to be Solved by the Invention

The straight-chain acyl carnitine penetrates the skin and produces excellent effects of stimulating the lipid metabolism. However, the straight-chain acyl group is liable to hydrolysis and is easily decomposed in water-based products that are a frequent form of external skin preparations, particularly cosmetics. Consequently, the products have poor storage stability and short life.

The present invention is directed to solving the problems as described above. It is therefore an object of the invention to provide external skin preparations and cosmetics that are excellent in storage stability, product life, skin affinity and percutaneous absorption properties.

It is another object of the invention to provide novel carnitine derivatives and salts thereof that are resistant to hydrolysis in the presence of aqueous media.

Means for Solving the Problems

The present inventors studied diligently and have found that α-branched acyl carnitine derivatives, particularly L-carnitine 2-hexyldecanoate, L-carnitine 2-methylpalmitate and L-carnitine 2-butyloctanoate, have superior stability in the presence of aqueous media. The present invention has been completed based on the finding. The present invention is concerned with the following [1] to [26].

[1]An external skin preparation comprising a carnitine derivative represented by Formula (1) and/or a salt of carnitine derivative represented by Formula (2):

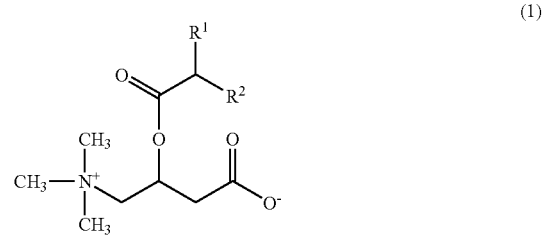

(1)

wherein $R^1$ and $R^2$ are each a saturated or unsaturated aliphatic hydrocarbon group of 1 to 18 carbon atoms that may have a branch;

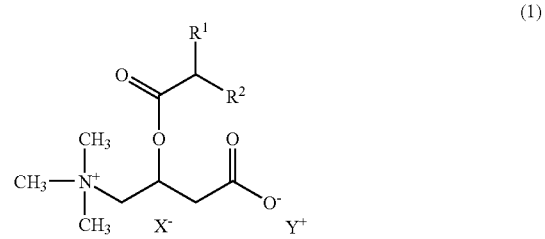

(1)

wherein $R^1$ and $R^2$ are as defined in Formula (1), $X^-$ is an inorganic or organic anion that maintains electrical neutrality with a cation part of the carnitine derivative, and $Y^+$ is an inorganic or organic cation that maintains electrical neutrality with an anion part of the carnitine derivative.

[2] The external skin preparation as described in [1], wherein $R^1$ and $R^2$ in Formulae (1) and (2) are each a saturated or unsaturated aliphatic hydrocarbon group of 3 to 16 carbon atoms that may have a branch.

[3] The external skin preparation as described in [1], wherein one of $R^1$ and $R^2$ in Formulae (1) and (2) is a linear alkyl group of 6 carbon atoms, and the other is a linear alkyl group of 8 carbon atoms.

[4] The external skin preparation as described in [1], wherein one of $R^1$ and $R^2$ in Formulae (1) and (2) is a linear alkyl group of 4 carbon atoms, and the other is a linear alkyl group of 6 carbon atoms.

[5] The external skin preparation as described in [1], wherein one of $R^1$ and $R^2$ in Formulae (1) and (2) is a methyl group, and the other is a linear alkyl group of 14 carbon atoms.

[6] The external skin preparation as described in any one of [1] to [5], wherein $X^-$ in Formula (2) is an anion selected from the group consisting of hydroxide ion, nitrate ion, sulfate ion, carbonate ion, hydrogen carbonate ion, halide ion, formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion.

[7] The external skin preparation as described in any one of [1] to [6], wherein $Y^+$ in Formula (2) is a cation selected from the group consisting of hydrogen ion, sodium ion, potassium ion, calcium ion, magnesium ion, zinc ion, ammonium ion, carnitine cation and carnitine derivative cation.

[8] The external skin preparation as described in any one of [1] to [7], wherein the carnitine derivative represented by Formula (1) and/or the salt of carnitine derivative represented by Formula (2) accounts for 0.01 to 20% by mass of the external skin preparation.

[9] A cosmetic comprising 0.01 to 20% by mass of the carnitine derivative and/or the salt of carnitine derivative described in any one of [1] to [7].

[10] The cosmetic as described in [9], which is a cosmetic for stimulating lipid metabolism.

[11] A carnitine derivative represented by Formula (3):

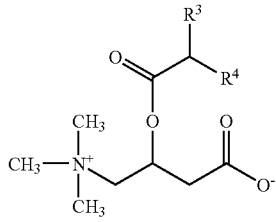

(3)

wherein one of $R^3$ and $R^4$ is a saturated aliphatic hydrocarbon group of 1 to 16 carbon atoms that may have a branch, and the other is a saturated aliphatic hydrocarbon group of 8 to 16 carbon atoms that may have a branch.

[12] A salt of carnitine derivative represented by Formula (4):

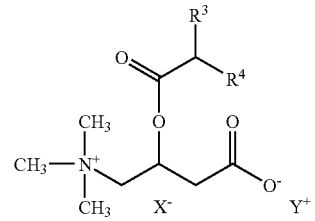

(4)

wherein one of $R^3$ and $R^4$ is a saturated aliphatic hydrocarbon group of 1 to 16 carbon atoms that may have a branch, the other is a saturated aliphatic hydrocarbon group of 8 to 16 carbon atoms that may have a branch, $X^-$ is an inorganic or organic anion that maintains electrical neutrality with a cation part of the carnitine derivative, and $Y^+$ is an inorganic or organic cation that maintains electrical neutrality with an anion part of the carnitine derivative.

[13] A carnitine derivative represented by Formula (5):

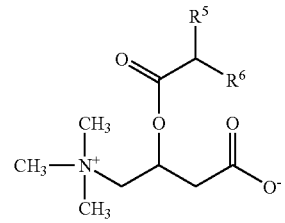

(5)

wherein one of $R^5$ and $R^6$ is a saturated aliphatic hydrocarbon group of 2 to 7 carbon atoms that may have a branch, and the other is a saturated aliphatic hydrocarbon group of 3 to 7 carbon atoms that may have a branch.

[14] A salt of carnitine derivative represented by Formula (6):

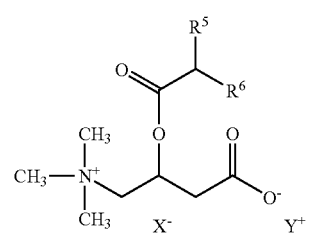

(6)

wherein one of $R^5$ and $R^6$ is a saturated aliphatic hydrocarbon group of 2 to 7 carbon atoms that may have a branch, the other is a saturated aliphatic hydrocarbon group of 3 to 7 carbon atoms that may have a branch, $X^-$ is an inorganic or organic anion that maintains electrical neutrality with a cation part of the carnitine derivative, and $Y^+$ is an inorganic or organic cation that maintains electrical neutrality with an anion part of the carnitine derivative.

[15] A carnitine derivative represented by Formula (7):

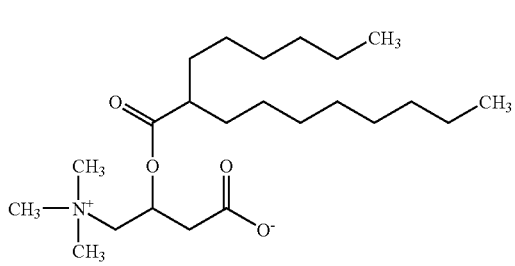

(7)

[16] A salt of carnitine derivative represented by Formula (8):

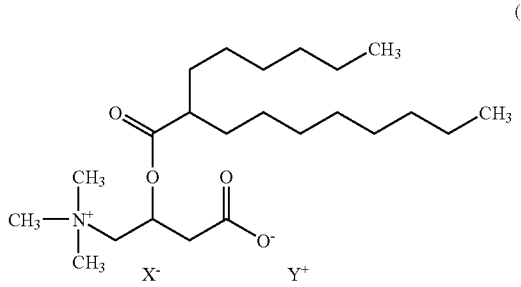

(8)

wherein $X^-$ is an inorganic or organic anion that maintains electrical neutrality with a cation part of the carnitine derivative, and $Y^+$ is an inorganic or organic cation that maintains electrical neutrality with an anion part of the carnitine derivative.

[17] The salt of carnitine derivative as described in [16], wherein $X^-$ in Formula (8) is an anion selected from the group consisting of hydroxide ion, nitrate ion, sulfate ion, carbonate ion, hydrogen carbonate ion, halide ion, formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion.

[18] The salt of carnitine derivative as described in [16] or [17], wherein $Y^+$ in Formula (8) is a cation selected from the group consisting of hydrogen ion, sodium ion, potassium ion, calcium ion, magnesium ion, zinc ion, ammonium ion, carnitine cation and carnitine derivative cation.

[19] A carnitine derivative represented by Formula (9):

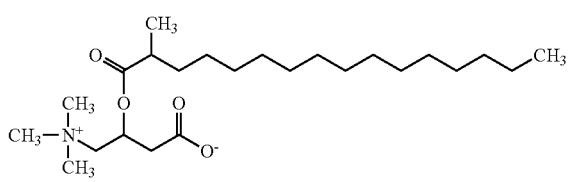

(9)

[20] A salt of carnitine derivative represented by Formula (10):

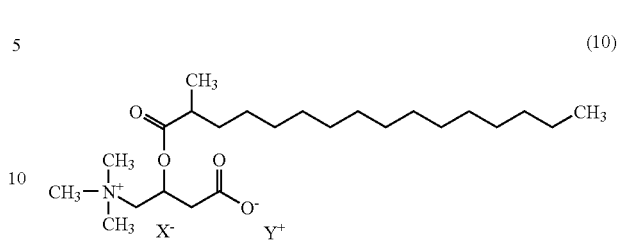

(10)

wherein $X^-$ is an inorganic or organic anion that maintains electrical neutrality with a cation part of the carnitine derivative, and $Y^+$ is an inorganic or organic cation that maintains electrical neutrality with an anion part of the carnitine derivative.

[21] The salt of carnitine derivative as described in [20], wherein $X^-$ in Formula (10) is an anion selected from the group consisting of hydroxide ion, nitrate ion, sulfate ion, carbonate ion, hydrogen carbonate ion, halide ion, formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion.

[22] The salt of carnitine derivative as described in [20] or [21], wherein $Y^+$ in Formula (10) is a cation selected from the group consisting of hydrogen ion, sodium ion, potassium ion, calcium ion, magnesium ion, zinc ion, ammonium ion, carnitine cation and carnitine derivative cation.

[23] A carnitine derivative represented by Formula (11):

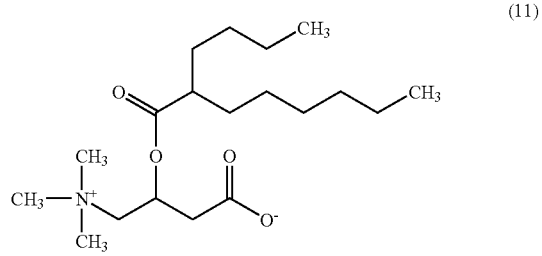

(11)

[24] A salt of carnitine derivative represented by Formula (12):

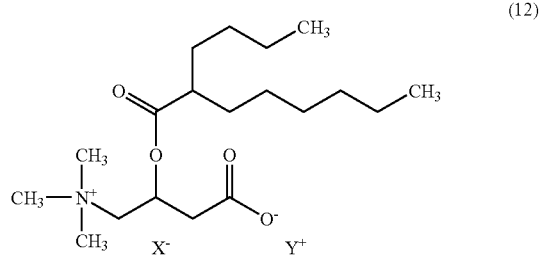

(12)

wherein $X^-$ is an inorganic or organic anion that maintains electrical neutrality with a cation part of the carnitine derivative, and $Y^+$ is an inorganic or organic cation that maintains electrical neutrality with an anion part of the carnitine derivative.

[25] The salt of carnitine derivative as described in [24], wherein $X^-$ in Formula (12) is an anion selected from the group consisting of hydroxide ion, nitrate ion, sulfate ion, carbonate ion, hydrogen carbonate ion, halide ion, formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion.

[26] The salt of carnitine derivative as described in [24] or [25], wherein $Y^+$ in Formula (12) is a cation selected from the group consisting of hydrogen ion, sodium ion, potassium ion, calcium ion, magnesium ion, zinc ion, ammonium ion, carnitine cation and carnitine derivative cation.

Effects of the Invention

The external skin preparations and cosmetics according to the present invention have long life because the carnitine derivatives resist decomposition in the presence of aqueous media. Consequently, the carnitine derivatives, and carnitine derivatives originating from the carnitine derivative salts in the products produce superior effects (skin affinity, percutaneous absorption properties, and lipid metabolism stimulating activity in tissues) stably over a long period.

Accordingly, the external skin preparations and cosmetics may be suitably used for stimulating lipid metabolism.

The novel carnitine derivatives and salts thereof according to the present invention are hardly hydrolyzed in the presence of aqueous media.

PREFERRED EMBODIMENTS OF THE INVENTION

Figure 1:
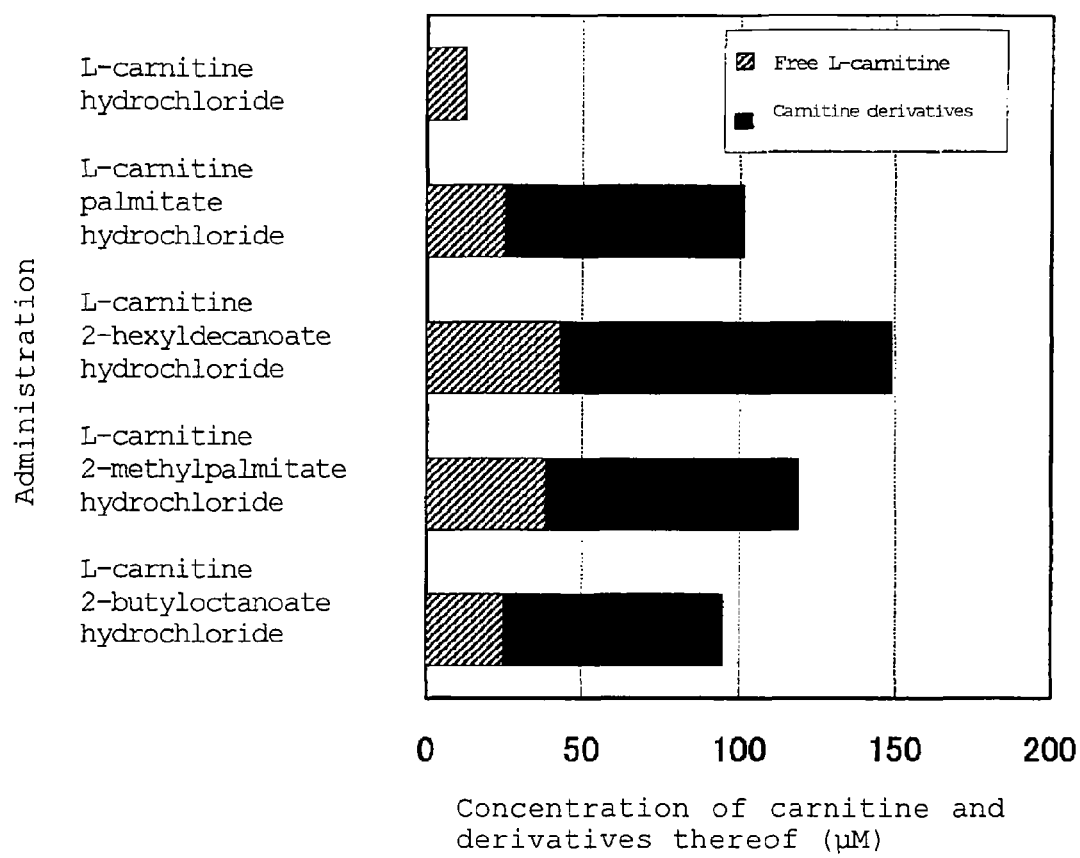
FIG. 1 is a graph showing concentrations of carnitine derivatives and free carnitine originating from the test substances that have passed to the dermis-side chamber after 24 hours in Example 1.

The present invention will be described in detail hereinbelow.

The external skin preparations and cosmetics of the present invention contain a specific carnitine derivative and/or a salt thereof. Namely, the external skin preparations and cosmetics may contain either or both of a specific carnitine derivative and a salt thereof.

<Carnitine Derivatives>

The carnitine derivatives used in the external skin preparations and cosmetics of the invention are represented by Formula (1):

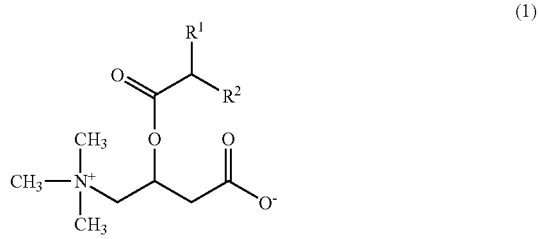

(1)

wherein $R^1$ and $R^2$ are each a saturated or unsaturated aliphatic hydrocarbon group of 1 to 18 carbon atoms that may have a branch. Preferably, one of $R^1$ and $R^2$ is a saturated or unsaturated aliphatic hydrocarbon group of 1 to 16 carbon atoms that may have a branch, and the other is a saturated or unsaturated aliphatic hydrocarbon group of 3 to 16 carbon atoms that may have a branch. More preferably, $R^1$ and $R^2$ are each a saturated or unsaturated aliphatic hydrocarbon group of 3 to 16 carbon atoms that may have a branch. Still preferably, $R^1$ and $R^2$ are each a saturated or unsaturated aliphatic hydrocarbon group of 4 to 12 carbon atoms that may have a branch.

The carnitine moiety in the carnitine derivatives is generally L-type. The carnitine derivatives contain an α-branched acyl group having $R^1$ and $R^2$. When $R^1$ and $R^2$ are different, the α-carbon atom at the branching point is an asymmetric carbon atom, and optical isomers result. The optical isomers are not particularly limited. Any optical isomers and mixtures of such isomers may be used in the invention.

The carnitine derivatives are stable for a long period probably because they contain an α-branched acyl group having $R^1$ and $R^2$, and the branched chain decreases electron donation to the ester bond to make hydrolysis of the acyl group difficult in the presence of aqueous media.

Examples of the saturated aliphatic hydrocarbon groups include linear or branched alkyl groups such as methyl, ethyl, n-propyl, isopropyl, n-butyl, isobutyl, sec-butyl, tert-butyl, n-pentyl, n-hexyl, 2-methylpentyl, 3-methylpentyl, 4-methylpentyl, 2-ethylbutyl, n-heptyl, 2-methylhexyl, 3-methylhexyl, 4-methylhexyl, 2-ethylpentyl, 3-ethylpentyl, n-octyl, 2-methylheptyl, 3-methylheptyl, 4-methylheptyl, 5-methylheptyl, 6-methylheptyl, 2-ethylhexyl, 3-ethylhexyl, 4-ethylhexyl, 2-propylpentyl, n-nonyl, n-decyl, n-undecyl, n-dodecyl, n-tridecyl, n-tetradecyl, n-pentadecyl, n-hexadecyl, n-heptadecyl, n-octadecyl and isostearyl.

Examples of the unsaturated aliphatic hydrocarbon groups include linear or branched alkenyl groups such as 10-undecenyl, 9-hexadecenyl, cis-9-octadecenyl, 11-octadecenyl, cis,cis-9,12-octadecadienyl, 9,12,15-octadecatrienyl, 6,9,12-octadecatrienyl and 9,11,13-octadecatrienyl.

Preferred combinations of $R^1$ and $R^2$ include methyl/methyl, methyl/ethyl, methyl/n-propyl, methyl/isopropyl, methyl/n-butyl, methyl/n-pentyl, methyl/n-hexyl, methyl/n-octyl, methyl/n-decyl, methyl/n-tetradecyl, methyl/n-hexadecyl, ethyl/ethyl, ethyl/n-propyl, ethyl/isopropyl, ethyl/n-butyl, ethyl/isopropyl, ethyl/n-butyl, ethyl/n-pentyl, ethyl/n-hexyl, ethyl/n-octyl, ethyl/n-decyl, ethyl/n-tetradecyl, ethyl/n-hexadecyl, n-propyl/n-propyl, n-propyl/n-butyl, n-propyl/n-pentyl, n-propyl/n-hexyl, n-butyl/n-hexyl, n-butyl/n-octyl and n-hexyl/n-octyl. The external skin preparations and cosmetics of the invention may contain one or more carnitine derivatives having different combinations of $R^1$ and $R^2$.

The embodiments of the carnitine derivatives represented by Formula (1) include known compounds and novel compounds. Representative novel carnitine derivatives will be described below.

The novel carnitine derivatives include compounds represented by Formula (3):

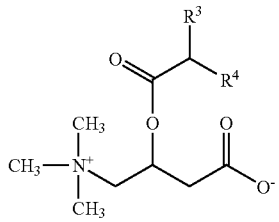
(3)

wherein one of $R^3$ and $R^4$ is a saturated aliphatic hydrocarbon group of 1 to 16 carbon atoms that may have a branch, and the other is a saturated aliphatic hydrocarbon group of 8 to 16 carbon atoms that may have a branch.

Examples of the saturated aliphatic hydrocarbon groups of 1 to 16 carbon atoms include linear or branched alkyl groups such as methyl, ethyl, n-propyl, isopropyl, n-butyl, isobutyl, sec-butyl, tert-butyl, n-pentyl, n-hexyl, 2-methylpentyl, 3-methylpentyl, 4-methylpentyl, 2-ethylbutyl, n-heptyl, 2-methylhexyl, 3-methylhexyl, 4-methylhexyl, 2-ethylpentyl, 3-ethylpentyl, n-octyl, 2-methylheptyl, 3-methylheptyl, 4-methylheptyl, 5-methylheptyl, 6-methylheptyl, 2-ethylhexyl, 3-ethylhexyl, 4-ethylhexyl, 2-propylpentyl, n-nonyl, n-decyl, n-undecyl, n-dodecyl, n-tridecyl, n-tetradecyl, n-pentadecyl and n-hexadecyl. Examples of the saturated aliphatic hydrocarbon groups of 8 to 16 carbon atoms include linear or branched alkyl groups such as n-octyl, 2-methylheptyl, 3-methylheptyl, 4-methylheptyl, 5-methylheptyl, 6-methylheptyl, 2-ethylhexyl, 3-ethylhexyl, 4-ethylhexyl, 2-propylpentyl, n-nonyl, n-decyl, n-undecyl, n-dodecyl, n-tridecyl, n-tetradecyl, n-pentadecyl and n-hexadecyl.

Different embodiments of the novel carnitine derivatives include compounds represented by Formula (5):

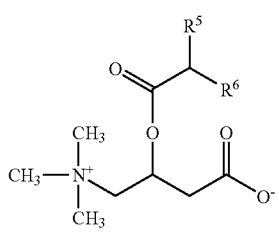
(5)

wherein one of $R^5$ and $R^6$ is a saturated aliphatic hydrocarbon group of 2 to 7 carbon atoms that may have a branch, and the other is a saturated aliphatic hydrocarbon group of 3 to 7 carbon atoms that may have a branch.

Examples of the saturated aliphatic hydrocarbon groups of 2 to 7 carbon atoms include linear or branched alkyl groups such as ethyl, n-propyl, isopropyl, n-butyl, isobutyl, sec-butyl, tert-butyl, n-pentyl, n-hexyl, 2-methylpentyl, 3-methylpentyl, 4-methylpentyl, 2-ethylbutyl, n-heptyl, 2-methylhexyl, 3-methylhexyl, 4-methylhexyl, 2-ethylpentyl and 3-ethylpentyl. Examples of the saturated aliphatic hydrocarbon groups of 3 to 7 carbon atoms include linear or branched alkyl groups such as n-propyl, isopropyl, n-butyl, isobutyl, sec-butyl, tert-butyl, n-pentyl, n-hexyl, 2-methylpentyl, 3-methylpentyl, 4-methylpentyl, 2-ethylbutyl, n-heptyl, 2-methylhexyl, 3-methylhexyl, 4-methylhexyl, 2-ethylpentyl and 3-ethylpentyl.

Preferred combinations of $R^5$ and $R^6$ in view of excellent skin affinity include ethyl/n-pentyl, ethyl/n-hexyl, ethyl/n-heptyl, n-propyl/n-butyl, n-propyl/n-pentyl, n-propyl/n-hexyl, n-propyl/n-heptyl, n-butyl/n-butyl, n-butyl/n-pentyl, n-butyl/n-hexyl, n-butyl/n-heptyl, n-pentyl/n-pentyl, n-pentyl/n-hexyl, n-pentyl/n-heptyl, n-hexyl/n-hexyl, n-hexyl/n-heptyl and n-heptyl/n-heptyl.

Preferably, one of $R^1$ and $R^2$ in Formula (1), or one of $R^3$ and $R^4$ in Formula (3) is a linear alkyl group of 6 carbon atoms, and the other is a linear alkyl group of 8 carbon atoms. That is, the carnitine derivative having the combination of n-hexyl and n-octyl, specifically L-carnitine 2-hexyldecanoate represented by Formula (7) below, is particularly preferable. This carnitine derivative is exceptionally stable in the presence of aqueous media.

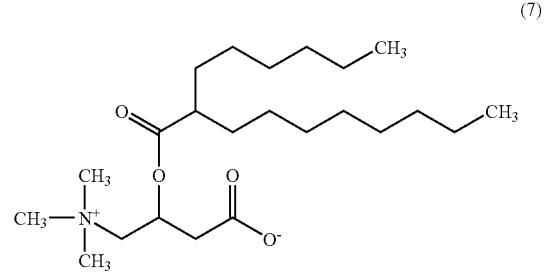
(7)

Also preferably, one of $R^1$ and $R^2$ in Formula (1), or one of $R^3$ and $R^4$ in Formula (3) is a methyl group, and the other is a linear alkyl group of 14 carbon atoms (n-tetradecyl group) Specifically, L-carnitine 2-methylpalmitate represented by Formula (9) below is preferable. Also preferably, one of $R^1$ and $R^2$ in Formula (1), or one of $R^5$ and $R^6$ in Formula (5) is a linear alkyl group of 4 carbon atoms, and the other is a linear alkyl group of 6 carbon atoms. That is, the carnitine derivative having the combination of n-butyl and n-hexyl, specifically L-carnitine 2-butyloctanoate represented by Formula (11) below, is preferable.

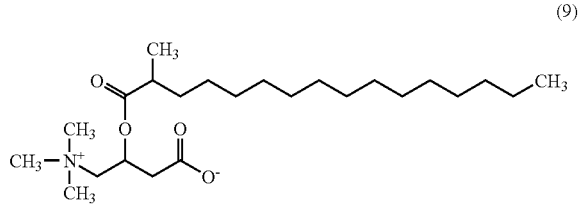
(9)

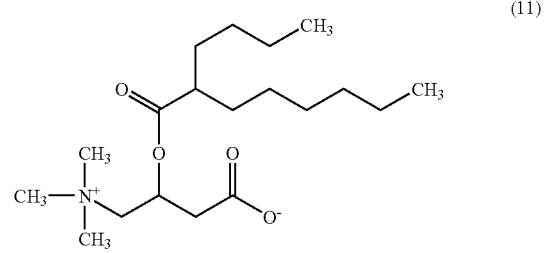
(11)

<Salts of Carnitine Derivatives>

The salts of carnitine derivatives used in the external skin preparations and cosmetics of the invention are represented by Formula (2):

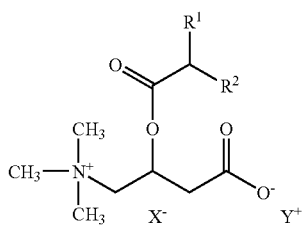

(2)

In Formula (2), X⁻ is an inorganic or organic anion that maintains electrical neutrality with a cation part of the carnitine derivative. Medically admissible anions are preferred, and examples thereof include inorganic ions such as hydroxide ion, nitrate ion, sulfate ion, carbonate ion, hydrogen carbonate ion and halide ion; and organic ions such as formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion. Of these, hydroxide ion, halide ion, citrate ion, carnitine anion and carnitine derivative anion are preferred in view of miscibility in external skin preparations, particularly cosmetics.

In Formula (2), Y⁺ is an inorganic or organic cation that maintains electrical neutrality with an anion part of the carnitine derivative. Medically admissible cations are preferred, and examples thereof include hydrogen ion, sodium ion, potassium ion, calcium ion, magnesium ion, zinc ion, ammonium ion, carnitine cation and carnitine derivative cation. Of these, hydrogen ion, sodium ion, potassium ion, carnitine cation and carnitine derivative cation are preferred in view of miscibility in external skin preparations, particularly cosmetics.

In Formula (2), $R^1$ and $R^2$ are as defined in Formula (1).

The external skin preparations and cosmetics of the invention may contain one or more salts of carnitine derivatives having different combinations of X⁻, Y⁺, $R^1$ and $R^2$.

The salts of carnitine derivatives represented by Formula (2) include known compounds and novel compounds. Representative novel salts of carnitine derivatives will be described below.

The embodiments of the novel salts of carnitine derivatives include compounds represented by Formula (4):

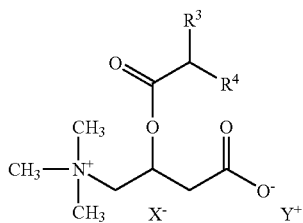

(4)

wherein $R^3$ and $R^4$ are as defined in Formula (3), and X⁻ and Y⁺ are as defined in Formula (2).

Different embodiments of the novel salts of carnitine derivatives include compounds represented by Formula (6):

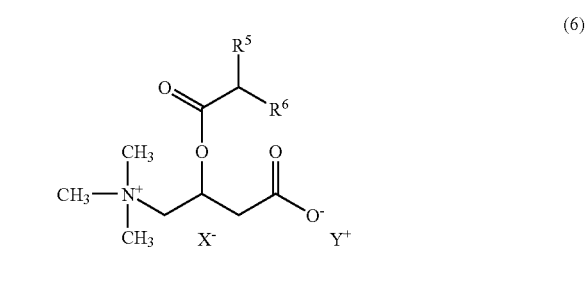

(6)

wherein $R^5$ and $R^6$ are as defined in Formula (5), and X⁻ and Y⁺ are as defined in Formula (2).

Preferably, one of $R^1$ and $R^2$ in Formula (2), or one of $R^3$ and $R^4$ in Formula (4) is a linear alkyl group of 6 carbon atoms, and the other is a linear alkyl group of 8 carbon atoms. That is, the salt of carnitine derivative having the combination of n-hexyl and n-octyl, specifically the salt of L-carnitine 2-hexyldecanoate represented by Formula (8) below, is particularly preferable. The carnitine derivative originating from this salt is exceptionally stable in the presence of aqueous media.

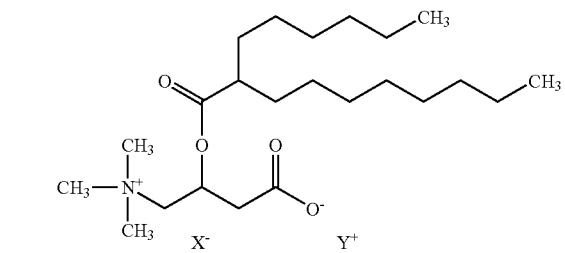

(8)

wherein X⁻ and Y⁺ are as defined in Formula (2).

Also preferably, one of $R^1$ and $R^2$ in Formula (2), or one of $R^3$ and $R^4$ in Formula (4) is a methyl group, and the other is a linear alkyl group of 14 carbon atoms (n-tetradecyl group) Specifically, the salt of L-carnitine 2-methylpalmitate represented by Formula (10) below is preferable. Also preferably, one of $R^1$ and $R^2$ in Formula (2), or one of $R^5$ and $R^6$ in Formula (6) is a linear alkyl group of 4 carbon atoms, and the other is a linear alkyl group of 6 carbon atoms. That is, the salt of carnitine derivative having the combination of n-butyl and n-hexyl, specifically the salt of L-carnitine 2-butyloctanoate represented by Formula (12) below, is preferable.

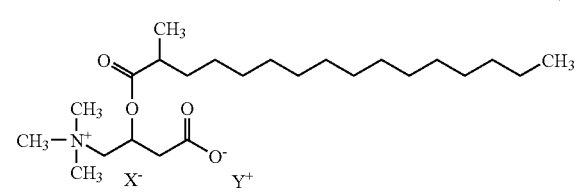

(10)

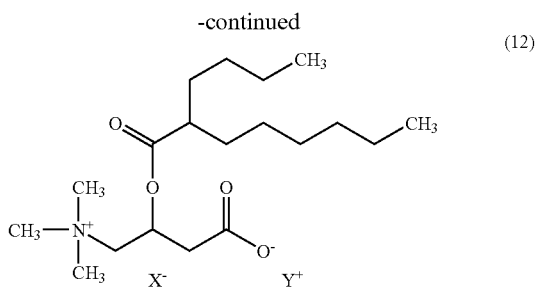

(12)

wherein X⁻ and Y⁺ are as defined in Formula (2).

<Production of Carnitine Derivatives and Salts Thereof>

The carnitine derivatives and salts thereof used in the external skin preparations and cosmetics of the invention may be synthesized from commercially available L-carnitines, for example by reaction of L-carnitines and fatty acid chlorides.

As an example, synthesis of L-carnitine 2-hexyldecanoate hydrochloride will be described below. L-carnitine and 2-hexyldecanoic acid chloride are mixed in trifluoroacetic acid, followed by heating and stirring at 50 to 80° C. to perform reaction. Thereafter, trifluoroacetic acid is distilled away by evaporation, and petroleum ether is added to the residue to recover the same, and water is added the residue to quench the acid chloride. Then, ethanol and diethyl ether is added to the residue to extract the same, and the water-ethanol phase is separated. The water-ethanol phase is combined with n-butanol and is washed with water as required. Then n-butanol is distilled away to obtain L-carnitine 2-hexyldecanoate hydrochloride.

Examples of the carnitines as raw materials for producing the carnitine derivatives and salts thereof include inner salts, inorganic salts such as hydrochlorides and sodium salts, and organic salts such as oxalates, tartrates and fumarates.

<External Skin Preparations and Cosmetics>

The external skin preparations and cosmetics, particularly lipid metabolism-improving cosmetics, contain the aforesaid carnitine derivatives and/or salts thereof. The lipid metabolism-improving cosmetics are the cosmetics which intend to improve and prevent skin problems and aging as well as obesity associated with excessive lipids and decreased lipid metabolism. Examples of the intended effects of the cosmetics include slimming, cellulite prevention, skin tightening, prevention of shiny and greasy skin and smeared makeup due to excessive sebum, improvement and prevention of seborrheic dermatitis and consequent hair loss, acne prevention, body odor prevention, and anti skin aging, skin activation and skin caring by promoting conversion of lipids into energy.

In the total amount of the external skin preparations, the carnitine derivative and/or salt thereof is generally contained in an amount of 0.01 to 20% by mass, preferably 0.05 to 12% by mass, more preferably 0.1 to 5% by mass. This amount indicates a content of the carnitine derivative or salt thereof when either is used singly, and a content of the carnitine derivative and salt thereof combined when they are used in combination.

When the external skin preparations contain the carnitine derivatives and/or salts thereof in the above amounts, the carnitine derivatives and/or salts thereof quickly penetrate the skin and produce effects as desired.

The cosmetics and lipid metabolism-improving cosmetics desirably contain the carnitine derivatives and/or salts thereof in amounts described above with respect to the external skin preparations.

The external skin preparations and cosmetics may contain other components common in general external skin preparations and cosmetics, while still achieving the effects of the invention.

Such components include:

hydrocarbons such as ozokerite, α-olefin oligomers, light isoparaffin, light liquid isoparaffin, squalene, squalane, synthetic squalane, vegetable squalane, ceresin, paraffin, polyethylene powder, polybutene, microcrystalline wax, liquid isoparaffin, liquid paraffin, mineral oil and vaseline;

natural fats and oils, such as natural waxes including jojoba oil, carnauba wax, candelilla wax, rice bran wax, shellac, lanolin, mink oil wax, whale wax, sugarcane wax, sperm oil, beeswax and montan wax; avocado oil, almond oil, olive oil, extra virgin olive oil, sesame oil, rice bran oil, rice oil, rice germ oil, corn oil, soybean oil, maize oil, persic oil, palm kernel oil, palm oil, castor oil, grape seed oil, cotton seed oil, coconut oil, hydrogenated coconut oil, beef tallow, hydrogenated oil, horse oil, mink oil, egg yolk oil, egg yolk fatty oil, rose hip oil, kukui nut oil, evening primrose oil, wheat germ oil, peanut oil, *camellia* oil, sasanqua oil, cacao butter, Japanese wax, beef bone fat, neatsfoot oil, lard, horse fat, mutton tallow, shea butter, *macadamia* nut oil and meadowfoam oil;

fatty acids such as lauric acid, myristic acid, palmitic acid, stearic acid, behenic acid, oleic acid, isostearic acid, 12-hydroxystearic acid, undecylenic acid and coconut fatty acid;

higher alcohols such as isostearyl alcohol, octyldodecanol, hexyldecanol, cholesterol, phytosterol, lauryl alcohol, myristyl alcohol, cetanol, stearyl alcohol, oleyl alcohol, behenyl alcohol and cetostearyl alcohol;

alkyl glyceryl ethers such as batyl alcohol, chimyl alcohol, selachyl alcohol and isostearyl glyceryl ether;

esters such as isopropyl myristate, butyl myristate, isopropyl palmitate, ethyl stearate, butyl stearate, ethyl oleate, ethyl linoleate, isopropyl linoleate, cetyl caprylate, hexyl laurate, isooctyl myristate, decyl myristate, myristyl myristate, cetyl myristate, octadecyl myristate, cetyl palmitate, stearyl stearate, decyl oleate, oleyl oleate, cetyl ricinoleate, isostearyl laurate, isotridecyl myristate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, octyldodecyl ricinoleate, ethyl isostearate, isopropyl isostearate, cetyl 2-ethylhexanoate, cetostearyl 2-ethylhexanoate, stearyl 2-ethylhexanoate, hexyl isostearate, ethylene glycol dioctanoate, ethylene glycol dioleate, propylene glycol dicaprylate, propylene glycol di(caprylate caprate), propylene glycol dicaprate, propylene glycol dioleate, neopentyl glycol dicaprate, neopentyl glycol dioctanoate, glyceryl tricaprylate, glyceryl tri-2-ethylhexanoate, glyceryl tri(caprylate caprate) glyceryl tri(caprylate caprate stearate), glyceryl triundecylate, glyceryl triisopalmitate, glyceryl triisostearate, trimethylolpropane tri-2-ethylhexanoate, trimethylolpropane triisostearate, pentaerythrityl tetra-2-ethylhexanoate, pentaerythrityl tetramyristate, pentaerythrityl tetraisostearate, diglyceryl tetraisostearate, octyldodecyl neopentanoate, isocetyl octanoate, isostearyl octanoate, 2-ethylhexyl isopelargonate, hexyldecyl dimethyloctanoate, octyldodecyl dimethyloctanoate, 2-ethylhexyl isopalmitate, isocetyl isostearate, isostearyl isostearate, octyldodecyl isostearate, lauryl lactate, myristyl lactate, cetyl lactate, octyldodecyl lactate, triethyl citrate, acetyltriethyl citrate, acetyltributyl citrate, trioctyl citrate, triisocetyl citrate, trioctyldodecyl citrate, diisostearyl malate, 2-ethylhexyl hydroxystearate, di-2-ethylhexyl succinate, diisopropyl adipate, diisobutyl adipate, dioctyl adipate, diheptylundecyl adipate, diethyl sebacate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate, isostearyl 12-stearoylhydroxystearate, polyoxyethylene (3) polyoxypropylene (1) cetyl ether acetate, polyoxyethylene (3) polyoxypropylene (1) isocetyl ether acetate, isononyl isononanoate, octyl isononanoate, tridecyl isononanoate and isotridecyl isononanoate;

silicone oils such as methyl polysiloxane, methylphenyl polysiloxane, methylhydrogen polysiloxane, methyl cyclopolysiloxane, octamethyl cyclotetrasiloxane, decamethyl cyclopentasiloxane, dodecamethyl cyclohexasiloxane, octamethyl trisiloxane, decamethyl tetrasiloxane, tetradecamethyl hexasiloxane, highly polymerized methyl polysiloxane, dimethyl siloxane/methyl(polyoxyethylene)siloxane/methyl(polyoxypropylene)siloxane copolymer, dimethyl siloxane/methyl(polyoxyethylene)siloxane copolymer, dimethyl siloxane/methyl(polyoxypropylene)siloxane copolymer, dimethyl siloxane/methyl cetyloxysiloxane copolymer, dimethyl siloxane/methyl stearoxysiloxane copolymer, polyether-modified silicones, alcohol-modified silicones, alkyl-modified silicones and amino-modified silicones;

polymers such as sodium alginate, carrageenan, agar, furcelleran, cyamoposis gum, *pyrus cyclonia* seed, konjac mannan, tamarind gum, tara gum, dextrin, locust bean gum, gum arabic, ghatti gum, karaya gum, tragacanth gum, arabinogalactan, pectin, marmelo, chitosan, starch, curdlan, xanthan gum, gellan gum, cyclodextrin, dextran, pullulan, microcrystalline cellulose, methylcellulose, ethylcellulose, hydroxyethylcellulose, hydroxypropylcellulose, hydroxypropylmethylcellulose, carboxymethylcellulose, carboxy starch, cationized cellulose, starch phosphate, cationized cyamoposis gum, carboxymethyl/hydroxypropylated cyamoposis gum, hydroxypropylated cyamoposis gum, albumin, casein, gelatin, sodium polyacrylate, polyacrylic acid amide, carboxyvinyl polymers, polyethyleneimine, highly polymerized polyethylene glycol, polyvinyl alcohol, polyvinylpyrrolidone, polyvinyl ether, polyacrylamide, acrylic acid copolymers, methacrylic acid copolymers, maleic acid copolymers, vinylpyridine copolymers, ethylene/acrylic acid copolymers, vinylpyrrolidone polymers, vinyl alcohol/vinylpyrrolidone copolymers, nitrogen-substituted acrylamide polymers, amino-modified silicones, cationized polymers, dimethylacryl ammonium polymers, acrylic acid-based anionic polymers, methacrylic acid-based anionic polymers, modified silicones, acrylic acid/alkyl($C_{10-30}$) methacrylate copolymer and polyoxyethylene/polyoxypropylene copolymer;

lower alcohols such as ethanol, isopropyl alcohol, 1-butanol, 2-butanol and benzyl alcohol;

polyhydric alcohols such as ethylene glycol, diethylene glycol, polyethylene glycol, propylene glycol, polypropylene glycol, glycerin, diglycerin, polyglycerin, 1,3-butanediol, triethylene glycol, dipropylene glycol, 3-methyl-1,3-butanediol, 1,2-pentanediol, 1,4-pentanediol, 1,5-pentanediol, 2,4-pentanediol, 2-methyl-2,4-pentanediol, 3-methyl-1,5-pentanediol, 1,2-hexanediol and 1,6-hexanediol;

anionic surfactants such as potassium coconut fatty acid, sodium coconut fatty acid, triethanolamine coconut fatty acid, potassium laurate, sodium laurate, triethanolamine laurate, potassium myristate, sodium myristate, isopropanolamine myristate, potassium palmitate, sodium palmitate, isopropanolamine palmitate, potassium stearate, sodium stearate, triethanolamine stearate, potassium oleate, sodium oleate, sodium castor oil fatty acid, zinc undecylenate, zinc laurate, zinc myristate, magnesium myristate, zinc palmitate, zinc stearate, calcium stearate, magnesium stearate, aluminum stearate, calcium myristate, magnesium myristate, aluminum dimyristate, aluminum isostearate, polyoxyethylene laurylether acetic acid, sodium polyoxyethylene laurylether acetate, polyoxyethylene tridecylether acetic acid, sodium polyoxyethylene tridecylether acetate, sodium stearoyl lactate, sodium isostearoyl lactate, lauroylsarcosine sodium, sarcosine coconut fatty acid, sarcosine sodium coconut fatty acid, sarcosine triethanolamine coconut fatty acid, lauroyl sarcosine, lauroyl sarcosine potassium, lauroyl sarcosine triethanolamine, oleoyl sarcosine, myristoyl sarcosine sodium, sodium stearoyl glutamate, coconut fatty acid acylglutamic acid, potassium coconut fatty acid acylglutamate, sodium coconut fatty acid acylglutamate, triethanolamine coconut fatty acid acylglutamate, lauroyl acylglutamic acid, potassium lauroyl acylglutamate, sodium lauroyl acylglutamate, triethanolamine lauroyl acylglutamate, myristoyl acylglutamic acid, potassium myristoyl acylglutamate, sodium myristoyl acylglutamate, stearoyl acylglutamic acid, potassium stearoyl acylglutamate, disodium stearoyl acylglutamate, sodium hydrogenated tallow fatty acid acylglutamate, sodium coconut fatty acid/hydrogenated tallow fatty acid acylglutamate, methylalanine sodium coconut fatty acid, lauroyl methylalanine, lauroyl methylalanine sodium, lauroyl methylalanine triethanolamine, myristoyl methylalanine sodium, lauroyl methyltaurine sodium, methyltaurine potassium coconut fatty acid, methyltaurine sodium coconut fatty acid, methyltaurine magnesium coconut fatty acid, myristoyl methyltaurine sodium, palmitoyl methyltaurine sodium, stearoyl methyltaurine sodium, oleoyl methyltaurine sodium, sodium alkanesulfonate, sodium tetradecenesulfonate, dioctylsodium sulfosuccinate, lauryl disodium sulfosuccinate, ethyl coconut fatty acid ester sodium sulfonate, sodium laurylsulfate, triethanolamine laurylsulfate, sodium cetyl sulfate, triethanolamine alkylsulfates (11, 13, 15), sodium alkylsulfates (12, 13), triethanolamine alkylsulfates (12, 13), ammonium alkylsulfates (12, 14, 16), diethanolamine alkylsulfates (12, 13), triethanolamine alkylsulfates (12-14), triethanolamine alkylsulfates (12-15), magnesium triethanolamine cocoalkylsulfate, ammonium laurylsulfate, potassium laurylsulfate, magnesium laurylsulfate, monoethanolamine laurylsulfate, diethanolamine laurylsulfate, sodium myristylsulfate, sodium stearylsulfate, sodium oleylsulfate, triethanolamine oleylsulfate, sodium polyoxyethylene laurylether sulfate, triethanolamine polyoxyethylene laurylether sulfate, sodium polyoxyethylene (1) alkyl (11, 13, 15) ether sulfate, triethanolamine polyoxyethylene (1) alkyl (11, 13, 15) ether sulfate, sodium polyoxyethylene (3) alkyl (11-15) ether sulfate, sodium polyoxyethylene (2) alkyl (12, 13) ether sulfate, sodium polyoxyethylene (3) alkyl (12-14) ether sulfate, sodium polyoxyethylene (3) alkyl (12-15) ether sulfate, sodium polyoxyethylene (2) laurylether sulfate, sodium polyoxyethylene (3) myristylether sulfate, sodium higher fatty acid alkanolamide sulfate, laurylphosphoric acid, sodium laurylphosphate, potassium cetylphosphate, diethanolamine cetylphosphate, polyoxyethylene oleylether phosphoric acid, polyoxyethylene laurylether phosphoric acid, sodium polyoxyethylene laurylether phosphate, polyoxyethylene cetylether phosphoric acid, sodium polyoxyethylene cetylether phosphate, polyoxyethylene stearylether phosphoric acid, polyoxyethylene oleylether phosphoric acid, sodium polyoxyethylene oleylether phosphate, polyoxyethylene alkylphenyl ether phosphoric acid, sodium polyoxyethylene alkylphenyl ether phosphate, triethanolamine polyoxyethylene alkylphenyl ether phosphate, polyoxyethylene octylether phosphoric acid, polyoxyethylene (10) alkyl (12, 13) ether phosphoric acid, polyoxyethylene alkyl (12-15) ether phosphoric acid, polyoxyethylene alkyl (12-16) ether phosphoric acid, triethanolamine polyoxyethylene laurylether phosphate and diethanolamine polyoxyethylene oleylether phosphate;

cationic surfactants such as dioctylamine, dimethylstearylamine, trilaurylamine, stearic acid diethylaminoethylamide, lauryltrimethylammonium chloride, cetyltrimethylammonium chloride, cetyltrimethylammonium bromide, cetyltrimethylammonium saccharin, stearyltrimethylammonium chloride, alkyl (20-22) trimethylammonium chloride, lauryltrimethylammonium bromide, alkyl (16, 18) trimethylammonium chloride, stearyltrimethylammonium bromide, stearyltrimethylammonium saccharin, alkyl (28) trimethylammonium chloride, di(polyoxyethylene)oleylmethylammonium chloride (2EO), dipolyoxyethylenestearylmethylammonium chloride, polyoxyethylene (1) polyoxypropylene (25) diethylmethylammonium chloride, tri(polyoxyethylene)stearylammonium chloride (5EO), distearyldimethylammonium chloride, dialkyl (12-15) dimethylammonium chloride, dialkyl (12-18) dimethylammonium chloride, dialkyl (14-18) dimethylammonium chloride, dicocoyldimethylammonium chloride, dicetyldimethylammonium chloride, isostearyllauryldimethylammonium chloride, benzalkonium chloride, myristyldimethylbenzylammonium chloride, lauryldimethyl(ethylbenzyl)ammonium chloride, stearyldimethylbenzylammonium chloride, laurylpyridinium chloride, cetylpyridinium chloride, lauroylcolaminoformylmethylpyridinium chloride, stearoylcolaminoformylmethylpyridinium chloride, alkylisoquinolium bromide, methylbenzethonium chloride and benzethonium chloride;

amphoteric surfactants such as 2-alkyl-N-carboxymethyl-N-hydroxyethyl imidazolinium betaine, alkyldiaminoethylglycine hydrochloride, lauryldiaminoethylglycine sodium, undecylhydroxyethylimidazolium betaine sodium, undecyl-N-carboxymethylimidazolium betaine, acyl-N-carboxyethyl-N-hydroxyethylethylenediamine disodium coconut fatty acid ester, acyl-N-carboxyethoxyethyl-N-carboxyethyl-ethylenediamine disodium coconut fatty acid ester, acyl-N-carboxymethoxyethyl-N-carboxymethylethylenediamine disodium coconut fatty acid ester, sodium laurylaminopropionate, sodium laurylaminodipropionate, triethanolamine laurylaminopropionate, acyl-N-carboxyethyl-N-hydroxyethyl-ethylenediamine sodium palm oil fatty acid ester, betaine lauryldimethylaminoacetate, betaine coconut oil alkyldimethylaminoacetate, betaine stearyldimethylaminoacetate, stearyldimethyl betaine sodium, amidopropylbetaine coconut fatty acid ester, amidopropylbetaine palm oil fatty acid ester, lauric acid amide betaine propylacetate, amidopropylbetaine ricinoleate, stearyldihydroxyethyl betaine and laurylhydroxysulfobetaine;

nonionic surfactants such as polyoxyethylene (10) alkyl (12, 13) ether, polyoxyethylene lauryl ether, polyoxyethylene cetyl ether, polyoxyethylene stearyl ether, polyoxyethylene oleyl ether, polyoxyethylene (3, 7, 12) alkyl (12-14) ether, polyoxyethylene tridecyl ether, polyoxyethylene myristyl ether, polyoxyethylene-sec-alkyl (14) ether, polyoxyethylene isocetyl ether, polyoxyethylene cetostearyl ether, polyoxyethylene (2, 10, 20) isostearyl ether, polyoxyethylene oleylcetyl ether, polyoxyethylene (20) arachyl ether, polyoxyethylene octyldodecyl ether, polyoxyethylene behenyl ether, polyoxyethylene octylphenyl ether, polyoxyethylene nonylphenyl ether, polyoxyethylene dinonylphenyl ether, polyoxyethylene (1) polyoxypropylene (1, 2, 4, 8) cetyl ether, polyoxyethylene (5) polyoxypropylene (1, 2, 4, 8) cetyl ether, polyoxyethylene (10) polyoxypropylene (1, 2, 4, 8) cetyl ether, polyoxyethylene (20) polyoxypropylene (1, 2, 4, 8) cetyl ether, polyoxyethylene polyoxypropylene lauryl ether, polyoxyethylene (3) polyoxypropylene (34) stearyl ether, polyoxyethylene (4) polyoxypropylene (30) stearyl ether, polyoxyethylene (34) polyoxypropylene (23) stearyl ether, polyoxyethylene polyoxypropylene cetyl ether, polyoxyethylene polyoxypropylene decyltetradecyl ether, polyethylene glycol monolaurate, ethylene glycol monostearate, polyethylene glycol monostearate, polyethylene glycol monooleate, ethylene glycol fatty acid ester, self-emulsifiable ethylene glycol monostearate, diethylene glycol laurate, polyethylene glycol myristate, polyethylene glycol palmitate, diethylene glycol stearate, self-emulsifiable polyethylene glycol (2) monostearate, polyethylene glycol isostearate, ethylene glycol dioctanoate, diethylene glycol dilaurate, polyethylene glycol dilaurate, polyethylene glycol (150) dipalmitate, ethylene glycol distearate, diethyleneglycol distearate, polyethylene glycol distearate, ethylene glycol dioleate, polyethylene glycol dioleate, polyethylene glycol diricinoleate, polyoxyethylene (20) sorbitan monolaurate, polyoxyethylene (20) sorbitan monopalmitate, polyoxyethylene (6) sorbitan monostearate, polyoxyethylene (20) sorbitan monostearate, polyoxyethylene (20) sorbitan tristearate, polyoxyethylene (6) sorbitan monooleate, polyoxyethylene (20) sorbitan monooleate, polyoxyethylene (20) sorbitan trioleate, sorbitan polyoxyethylene (20) coconut fatty acid ester, polyoxyethylene (10-80) sorbitan monolaurate, polyoxyethylene sorbitan tristearate, polyoxyethylene (20) sorbitan isostearate, polyoxyethylene (150) sorbitan tristearate, polyoxyethylene castor oil, polyoxyethylene hydrogenated castor oil, polyoxyethylene (10) hydrogenated castor oil, polyoxyethylene (20) hydrogenated castor oil, polyoxyethylene (40) hydrogenated castor oil, polyoxyethylene (50) hydrogenated castor oil, polyoxyethylene (60) hydrogenated castor oil, lipophilic glyceryl monostearate, lipophilic glyceryl monooleate, self-emulsifiable glyceryl monostearate, coconut fatty acid glyceryl, glyceryl laurate, glyceryl myristate, glyceryl isostearate, glyceryl ricinoleate, glyceryl monohydroxystearate, glyceryl oleate, glyceryl linoleate, glyceryl erucate, glyceryl behenate, wheat germ oil fatty acid glyceride, safflower oil fatty acid glyceryl, hydrogenated soybean fatty acid glyceryl, saturated fatty acid glyceride, cotton seed oil fatty acid glyceryl, monoisostearic acid glyceryl monomyristate, monotallow fatty acid glyceride, monoglyceryl lanolin fatty acid, glyceryl sesquioleate, glyceryl distearate, glyceryl diisostearate, glyceryl diarachidate, sorbitan monolaurate, sorbitan monopalmitate, sorbitan monostearate, sorbitan monoisostearate, sorbitan monooleate, sorbitan sesquistearate, sorbitan sesquioleate, sorbitan tristearate, sorbitan trioleate, coconut fatty acid sorbitan, sorbitan isostearate, sorbitan sesquiisostearate, sorbitan distearate, diglyceryl isopalmitate, poly (4-10) glyceryl monolaurate, poly (10) glyceryl monomyristate, poly (2-10) glyceryl monostearate, poly (2-10) glyceryl monoisostearate, poly (2-10) glyceryl monooleate, diglyceryl sesquioleate, poly (2-10) glyceryl diisostearate, poly (6-10) glyceryl distearate, diglyceryl triisostearate, poly (10) glyceryl tristearate, poly (10) glyceryl trioleate, poly (2) glyceryl tetraisostearate, decaglyceryl pentastearate, poly (6-10) glyceryl pentaoleate, poly (10) glyceryl heptastearate, decaglyceryl decastearate, poly (10) glyceryl decaoleate, condensed poly (6) glyceryl ricinoleate, cane sugar fatty acid ester, cane sugar coconut fatty acid ester, alkyl glucoside, coconut oil alkyldimethylamine oxide, lauryldimethylamine oxide, dihydroxyethyllauryldimethylamine oxide, stearyldimethylamine oxide, oleyldimethylamine oxide and polyoxyethylene coconut oil alkyldimethylamine oxide;

natural surfactants such as saponin, lecithin, soybean phospholipid, hydrogenated, soybean phospholipid, soybean lysophospholipid, hydrogenated soybean lysophospholipid, egg yolk lecithin, hydrogenated egg yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid and mannosylerythritol lipid;

ultraviolet light absorbers, including paraaminobenzoic acid, paraaminobenzoic acid derivatives such as ethyl paraaminobenzoate, glyceryl paraaminobenzoate, amyl paradimethylaminobenzoate and 2-ethylhexyl paradimethylaminobenzoate, cinnamic acid derivatives such as benzyl cinnamate, glyceryl diparamethoxycinnamate mono-2-ethylhexanoate, methyl 2,4-diisopropylcinnamate, ethyl 2,4-diisopropylcinnamate, potassium paramethoxycinnamate, sodium paramethoxycinnamate, isopropyl paramethoxycinnamate, 2-ethylhexyl paramethoxycinnamate, 2-ethoxyethyl paramethoxycinnamate and ethyl paraethoxycinnamate, urocanic acid, urocanic acid derivatives such as ethyl urocanate.

benzophenone derivatives such as 2,4-dihydroxybenzophenone, 2,2', 4,4'-tetrahydroxybenzophenone, 2-hydroxy-4-methoxy-5-sulfobenzophenonesodium, 2-hydroxy-4-methoxybenzophenone-5-sulfonic acid, 2-hydroxy-4-methoxybenzophenone, 2,2'-dihydroxy-4,4'-dimethoxybenzophenone and 2,2'-dihydroxy-4,4'-dimethoxy-5-sulfobenzophenonesodium, salicylic acid derivatives such as ethylene glycol salicylate, 2-ethylhexyl salicylate, phenyl salicylate, benzyl salicylate, p-tert-butylphenyl salicylate, homomethyl salicylate and 3,3,5-trimethylcyclohexyl salicylate, 2-(2'-hydroxy-5'-methoxyphenyl)benzotriazole and 4-tert-butyl-4'-methoxybenzoylmethane;

powders and color materials such as kaolin, silicic anhydride, aluminum magnesium silicate, sericite, talc, boron nitride, mica, montmorillonite, hemp cellulose powder, wheat starch, silk powder, cornstarch, nitro dye, azo dye, nitroso dye, triphenylmethane dye, xanthene dye, quinoline dye, anthraquinone dye, indigo dye, pyrene dye, phthalocyanine dye, natural dyes including flavonoid, quinone, porphyrin, water-soluble annatto, squid ink powder, caramel, guaiazulene, gardenia blue, gardenia yellow, cochineal, shikonin, copper chlorophyllin sodium, paprika dye, safflower red, safflower yellow, laccaic acid and riboflavin butyrate, carbon black, yellow iron oxide, black iron oxide, red iron oxide, iron blue, ultramarine blue, zinc oxide, chromium oxide, titanium oxide, black titanium oxide, zirconium oxide, chromium hydroxide, alumina, magnesium oxide, barium sulfate, aluminum hydroxide, calcium carbonate, lithium cobalt titanate, manganese violet and pearl pigment;

plant extracts such as *angelica keiskei* extract, gambir extract, avocado extract, *hydrangea serrata* leaf extract, *gynostemma pentaphyllum* extract, althea extract, *arnica* extract, oil-soluble *arnica* extract, almond extract, *aloe* extract, *styrax benzoin* resin extract, *ginkgo* extract, *urtica* extract, orris root extract, fennel extract, turmeric extract, rose fruit extract, *echinacea* leaf extract, *scutellaria baicalensis* root extract, *phellodendron* bark extract, *coptis* rhizome extract, *hordeum vulgare* seed extract, gumbo extract, *hypericum erectum* extract, oil-soluble *hypericum erectum* extract, *lamium album* flower extract, oil-soluble *lamium album* flower extract, *ononis* extract, *nasturtium officinale* extract, orange flower water, kaki tannin, puerariae radix extract, *valerian* extract, cattail extract, *chamomilla* extract, oil-soluble *chamomilla* extract, *chamomilla* water, oat extract, carrot extract, oil-soluble carrot extract, carrot oil, *artemisia capillaris* extract, licorice extract, licorice extract powder, licorice flavonoid, *cantharis* tincture, raspberry extract, kiwi extract, *cinchona* bark extract, cucumber extract, apricot kernel extract, quince seed extract, *gardenia* extract, *sasa veitchii* extract, *sophora angustifolia* extract, walnut shell extract, *clematis* extract, brown sugar extract, *chlorella* extract, mulberry extract, cinnamon bark extract, *gentian* extract, *geranium* herb extract, tea extract, spatterdock extract, *arctium lappa* root extract, oil-soluble *arctium lappa* root extract, wheat germ extract, hydrolyzed wheat powder, rice bran extract, rice bran fermentation extract, comfrey extract, *asiasarum* root extract, saffron extract, *saponaria officinalis* extract, oil-soluble *salvia* extract, *crataegus cuneata* fruit extract, *xanthoxylum* extract, shiitake mushroom extract, shiitake mushroom extract powder, *rehmannia glutinosa* extract, sycon extract, oil-soluble sycon extract, Japanese basil extract, linden extract, oil-soluble linden extract, *filipendula multijuga* extract, crude drug extract, *coix lacryma-jobi* seed extract, ginger extract, oil-soluble ginger extract, ginger tincture, *acorus calamus* root extract, *betula alba* extract, oil-soluble *betula alba* extract, *betula alba* sap, *lonicera* extract, *equisetum arvense* extract, oil-soluble *equisetum arvense* extract, scordinin, *stevia* extract, ivy extract, *crataegus oxyacantha* extract, *sambucus nigra* flower extract, *juniperus communis* extract, *achillea millefolium* extract, oil-soluble *achillea millefolium* extract, *mentha piperita* extract, sage extract, oil-soluble sage extract, sage water, *malva sylvestris* extract, celery extract, *cnidium officinale* extract, *cnidium officinale* water, *swertia japonica* extract, soybean extract, jujube extract, thyme extract, *camellia sinensis* leaf extract, *camellia sinensis* dry distillate, *camellia sinensis* seed extract, clove flower extract, *citrus unshiu* peel extract, *camellia japonica* seed extract, *centella asiatica* extract, oil-soluble *juglans regia* extract, duke extract, *terminalia* extract, *angelica acutiloba* extract, oil-soluble *angelica acutiloba* extract, *angelica acutiloba* water, *calendula officinalis* flower extract, oil-soluble *calendula officinalis* flower extract, soymilk powder, *prunus persica* extract, *citrus aurantium amara* extract, *houttuynia cordata* extract, tomato extract, *potentilla erecta* root extract, natto extract, ginseng extract, oil-soluble ginseng extract, garlic extract, *rosa canina* fruit extract, oil-soluble *rosa canina* fruit extract, malt extract, malt root extract, *ophiopogon* tuber extract, parsley extract, *hordeum vulgare* leaf juice concentrate, distilled peppermint water, *hamamelis* water, *hamamelis* extract, *rosa centifolia* flower extract, *parietaria* extract, *isodonis japonicus* extract, *eriobotrya japonica* leaf extract, oil-soluble *eriobotrya japonica* leaf extract, coltsfoot flower extract, *poria cocos* extract, *ruscus aculeatus* root extract, *ruscus aculeatus* root extract powder, grape extract, grape leaf extract, grape water, hayflower extract, *luffa cylindrica* fruit extract, *luffa cylindrica* fruit water, safflower extract, oil-soluble *tilia miqueliana* extract, *tilia miqueliana* water, *paeonia suffruticosa* root extract, hops extract, oil-soluble hops extract, *pinus sylvestris* cone extract, *silybum marianum* fruit extract, horse chestnut extract, oil-soluble horse chestnut extract, *sapindus mukurossi* peel extract, *melissa officinalis* leaf extract, *melilotus officinalis* extract, peach leaf extract, oil-soluble peach leaf extract, bean-sprouts extract, *centaurea cyanus* flower extract, *centaurea cyanus* flower water, *eucalyptus* extract, *saxifraga sarmentosa* extract, *lilium candidum* bulb extract, *coix lacryma jobi* seed extract, oil-soluble *coix lacryma jobi* seed extract, *artemisia princeps* extract, *artemisia princeps* water, lavender extract, lavender water, apple extract, *ganoderma lucidum* extract, lettuce extract, *astragalus sinicus* extract, rose water, rosemary extract, oil-soluble rosemary extract, *anthemis nobilis* flower extract and *sanguisorba officinalis* root extract;

amino acids and peptides such as glycine, valine, leucine, isoleucine, serine, threonine, phenylalanine, tyrosine, tryptophan, cystine, cysteine, methionine, hydroxyproline, aspartic acid, asparagine, glutamic acid, glutamine, histidine, γ-aminobutyric acid, DL-pyrrolidonecarboxylic acid, ε-aminocaproic acid, hydrolyzed elastin, water-soluble elastin, hydrolyzed collagen, water-soluble collagen, casein, glutathione, wheat peptide and soybean peptide;

vitamins and vitamin affecters, including vitamin A such as retinol, retinal, retinoic acid, retinol acetate and retinol palmitate, carotenoids such as α-carotene, β-carotene, γ-carotene, δ-carotene, lycopene, zeaxanthin, cryptoxanthin, echinenone and astaxanthin, vitamin B1 such as thiamines, vitamin B2 such as riboflavin, vitamin B6 such as pyridoxine, pyridoxal and pyridoxamine, vitamin B12 such as cyanocobalamin, folic acids, nicotinic acid, nicotinic acid amide, pantothenic acids, biotins, vitamin C such as L-ascorbic acid, sodium L-ascorbate, L-ascorbyl stearate, L-ascorbyl palmitate, L-ascorbyl dipalmitate, L-ascorbyl tetraisopalmitate, disodium L-ascorbate sulfate, magnesium L-ascorbate, L-ascorbyl sodium phosphate, ascorbic acid-2-phosphate and L-ascorbic acid-2-glucoside, vitamin D such as ergocalciferol and cholecalciferol, vitamin E such as d-α-tocopherol, DL-α-tocopherol, dl-α-tocopherol acetate, dl-α-tocopherol succinate, β-tocopherol, γ-tocopherol and d-δ-tocopherol, ubiquinones, vitamin K, carnitine, ferulic acid, γ-oryzanol, α-lipoic acid and orotic acid;

antiseptics such as benzoic acid, sodium benzoate, undecylenic acid, salicylic acid, sorbic acid, potassium sorbate, dehydroacetic acid, sodium dehydroacetate, isobutyl paraoxybenzoate, isopropyl paraoxybenzoate, ethyl paraoxybenzoate, butyl paraoxybenzoate, propyl paraoxybenzoate, benzyl paraoxybenzoate, methyl paraoxybenzoate, methyl sodium paraoxybenzoate, phenoxyethanol, photosensitive agent No. 101, photosensitive agent No. 201 and photosensitive agent No. 401;

antioxidants such as butylhydroxyanisole, butylhydroxytoluene, propyl gallate, erythorbic acid, sodium erythorbate, parahydroxyanisole and octyl gallate;

sequestrant including metal ionic compounds such as trisodium ethylenediaminehydroxyethyltriacetate, edetic acid, disodium edetate, trisodium edetate, tetrasodium edetate, sodium citrate, gluconic acid, phytic acid, sodium polyphosphate and sodium metaphosphate;

moisturizers such as hyaluronic acid, sodium hyaluronate, sodium chondroitinsulfate, sodium lactate, sodium pyrrolidonecarboxylate, betaine, lactic acid bacteria culture solution, yeast extract and ceramide;

anti-inflammatory agents such as glycyrrhizinic acid, trisodium glycyrrhizinate, dipotassium glycyrrhizinate, monoammonium glycyrrhizinate, β-glycyrrhetinic acid, glyceryl glycyrrhetinate, stearyl glycyrrhetinate, lysozyme chloride, hydrocortisone and allantoin;

pH adjusters such as sodium hydroxide, potassium hydroxide and triethanolamine;

salts such as sodium chloride, potassium chloride, magnesium chloride and sodium sulfate;

α-hydroxy acids such as citric acid, glycolic acid, tartaric acid and lactic acid;

whitening agents such as arbutin, α-arbutin and placental extract;

essential oils such as *angelica* oil, ylang ylang oil, elemi oil, German chamomile oil, *anthemis nobilis* oil, cardamom oil, *calamus* oil, galbanum oil, camphor oil, carrot seed oil, clary sage oil, clove oil, cinnamon bark oil, coriander oil, cypress oil, sandalwood oil, cedarwood oil, *citronella* oil, cinnamon leaf oil, jasmine absolute, juniper berry oil, ginger extract, spearmint oil, sage oil, cedar oil, *geranium* oil, thyme oil, tea tree oil, nutmeg oil, niaouli oil, neroli oil, pine oil, basil oil, peppermint oil, patchouli oil, palmarosa oil, fennel oil, petitgrain oil, black pepper oil, frankincense oil, vetivert oil, peppermint oil, bergamot oil, benzoin oil, *aniba rosaeodora* oil, marjoram oil, myrrh oil, *melissa* oil, *eucalyptus* oil, *ravensara* oil, lavandin oil, lavender oil, lindane oil, rose oil, rosewood oil, rosemary oil and lovage oil;

terpenes such as pinene, terpinene, terpinolene, myrcene and longifolene;

perfumes and water.

The formulations and forms of the external skin preparations and cosmetics are not particularly limited as long as they are used directly on skin. It is more preferable that the external skin preparations and cosmetics be applied to the skin in the vicinity of where subcutaneous fat metabolism is desired. In the broad sense, the external skin preparations and cosmetics include any formulations that are used directly on skin, such as skin milks, skin creams, foundation creams, massage creams, cleansing creams, shaving creams, cleansing foams, skin toners, lotions, packs, lipsticks, rouges, eye shadows, manicures, soaps, body shampoos, hand soaps, shampoos, conditioners, hair tonics, treatment conditioners, hair creams, hair sprays, hair growth tonics, baldness remedies, hairdyes, styling spritz, depilatories, antidandruff agents, toothpastes, denture adhesives, mouthwashes, permanent waving agents, curling agents, styling agents, ointments, adhesive skin patches, taping agents, bath agents, antiperspirants and sunscreen agents. The external skin preparations and cosmetics may be used regardless of user's gender and age, and may be used for animal skin as well as human skin.

The external skin preparations and cosmetics according to the present invention may be in any forms including solids, liquids, semisolids, gases, powders, granules, tablets, gels and foams.

Although not compulsory, the formulations and forms including aqueous media are preferably selected because the present invention is particularly effective in improving poor stability of the conventional carnitine derivatives and salts thereof in aqueous preparations. In this case, water may suitably account for 0.01 to 99.99% by mass of the external skin preparations or cosmetics.

The cosmetics according to the present invention may further contain existing cosmetic ingredients other than the aforesaid components while still achieving the effects of the invention. Examples of such ingredients include those listed in The Japanese Standards of Cosmetic Ingredients 2nd edition (edited by Society of Japanese Pharmacopoeia and published by Yakuji Nippo, Ltd. (1984)), The Japanese Cosmetic Ingredients Codex (edited by Ministry of Health and Welfare, Pharmaceutical Examination Division and published by Yakuji Nippo, Ltd. (1993)), Supplement to The Japanese Cosmetic Ingredients Codex (edited by Ministry of Health and Welfare, Pharmaceutical Examination Division and published by Yakuji Nippo, Ltd. (1993)), The Comprehensive Licensing Standards of Cosmetics by Category (edited by Ministry of Health and Welfare, Pharmaceutical Examination Division and published by Yakuji Nippo, Ltd. (1993)), The Japanese Cosmetic Ingredients Codex by Category (edited by Ministry of Health and Welfare, Pharmaceutical Examination Division and published by Yakuji Nippo, Ltd. (1997)), Dictionary of Cosmetic Ingredients (Nikko Chemicals., Co. Ltd. (1991)), and 300 Latest Cosmetic Functional Materials (CMS Publishing Co., Ltd. (2002)).

The external skin preparations and cosmetics of the present invention may be produced by common methods depending on the formulations, for example by dissolving, mixing or dispersing the aforesaid ingredients in predetermined amounts.

The present invention will be described in greater detail by examples below. However, it should be construed that the invention is not limited to such examples. In Examples, % is by mass unless otherwise mentioned.

EXAMPLES

Synthetic Example 1

Synthesis of L-carnitine 2-hexyldecanoate hydrochloride

In an ice bath, 45.6 g (0.283 mol) of L-carnitine was dissolved in 150 ml of trifluoroacetic acid. To the resultant solution, 116.6 g (0.425 mol) of 2-hexyldecanoic acid chloride was added dropwise over a period of 10 minutes, followed by heating and stirring at 80° C. for 4 hours. The solvent was distilled off under reduced pressure. The resultant dark brown oily substance weighing 264.6 g was washed with 200 ml of n-hexane three times, and 200 ml of a black oily substance was collected. 3.0 g of the oily substance was subjected to extraction with 20 ml of ethanol, 30 ml of n-butanol, and 60 ml of water. The organic phase obtained was washed with 60 ml of water, and with a mixture of 20 ml of ethanol and 60 ml of water. The organic phase was washed with 60 ml of water, collected and dried. Distilling away the solvent resulted in 2.0 g of L-carnitine 2-hexyldecanoate hydrochloride.

The structure of the compound obtained was identified by NMR, liquid chromatography-mass spectroscopy (LC/MS) and elemental analysis.

<NMR>
$^1$H-NMR (CDCl$_3$): 0.90 ppm (6H, t, 7.0 Hz), 1.29-1.62 ppm (24H, m), 2.41 ppm (1H, m), 2.76 ppm (2H, d, 6.0 Hz), 3.21 ppm (9H, s), 3.75 ppm (1H, d, 14.6 Hz), 3.92 ppm (1H, dd, 8.2, 14.6 Hz), 5.60-5.64 ppm (1H, m)

NMR apparatus: Burker Advance 500

Sample concentration: 40 mg sample/422 mg heavy chloroform

Temperature: ambient

<Liquid Chromatography-Mass Spectroscopy (LC/MS)>
MS (ESI) m/z: 400.5 [M$^+$] (LC/MS)

Liquid chromatograph (LC): Agilent 1100 series

Column: Shodex silica C8-5B

Column temperature: 40° C.

Eluting solution: 20 mM aqueous ammonium acetate solution/acetonitrile (30/70)

Flow rate: 1.0 ml/min

Sample concentration and injection amount: 10 μl×5 mg/ml eluting solution

Detection: photodiode array UV 200-700 nm

Mass spectrometer (MS): Thermoquest LCQ Advantage

Ionizing method: ESI (electrospray ionization)

Scan range: m/z 50-1000 (alternate positive and negative charges)

MS/MS collision energy: 40%

<Elemental Analysis>
Elemental analysis: C, 62.8%, H, 10.6%, N, 3.5%, O, 14.9%, Cl, 8.2%.

C, H, N and O: Organic elemental analyzer CHNS-932 and oxygen analysis option VTF-900 (manufactured by LECO)

References: sym-diphenylthiourea (for analysis of C, H and N), and p-nitroaniline (for analysis of O)

Cl: ion chromatography (Exactly 1 mg of the sample was mixed with an eluting solution (1.8 mM Na$_2$CO$_3$+1.7 mM NaHCO$_3$) to a constant volume of 100 ml, and analyzed with an anion chromatograph (DIONEX DX-500) to determine Cl in the sample.)

Column: Shodex SI-90 4E

Flow rate: 1.0 ml/min

Injection amount: 25 μl

Detector: Electrical conductivity detector

Suppressor: ASRS-I

Synthetic Example 2

Synthesis of L-carnitine 2-methylpalmitate hydrochloride

In an ice bath, 45.6 g (0.283 mol) of L-carnitine was dissolved in 150 ml of trifluoroacetic acid. To the resultant solution, 122.4 g (0.425 mol) of 2-methylpalmitic acid chloride was added dropwise over a period of 10 minutes, followed by heating and stirring at 80° C. for 4 hours. The solvent was distilled off under reduced pressure. The resultant dark brown oily substance weighing 278.0 g was washed with 200 ml of n-hexane three times, and 200 ml of a black oily substance was collected. 3.0 g of the oily substance was subjected to extraction with 20 ml of ethanol, 30 ml of n-butanol, and 60 ml of water. The organic phase obtained was washed with 60 ml of water, and with a mixture of 20 ml of ethanol and 60 ml of water. The organic phase was washed with 60 ml of water, collected and dried. Distilling away the solvent resulted in 2.2 g of L-carnitine 2-methylpalmitate hydrochloride.

The structure of the compound obtained was identified by NMR, liquid chromatography-mass spectroscopy (LC/MS) and elemental analysis as described in Synthetic Example 1.

<NMR>
$^1$H-NMR (CDCl$_3$): 2.50 ppm (1H, m), 2.75 ppm (1H, dd, 6.2, 1.5 Hz), 2.80 ppm (1H, m), 3.73 ppm (1H, d, 14.4 Hz), 3.91 ppm (1H, dd, 14.4, 8.5 Hz), 5.61-5.65 ppm (1H, m)

<Liquid Chromatography-Mass Spectroscopy (LC/MS)>
MS (ESI) m/z: 414.5 [M$^+$]

<Elemental Analysis>
C, 64.3%, H, 10.3%, N, 3.2%, O, 14.2%, Cl, 8.0%.

Synthetic Example 3

Synthesis of L-carnitine 2-butyloctanoate hydrochloride

In an ice bath, 45.6 g (0.283 mol) of L-carnitine was dissolved in 150 ml of trifluoroacetic acid. To the resultant solution, 92.7 g (0.425 mol) of 2-butyloctanoic acid chloride was added dropwise over a period of 10 minutes, followed by heating and stirring at 80° C. for 4 hours. The solvent was distilled off under reduced pressure. The resultant dark brown oily substance weighing 250.0 g was washed with 200 ml of n-hexane three times, and 200 ml of a black oily substance was collected. 3.0 g of the oily substance was subjected to extraction with 20 ml of ethanol, 30 ml of n-butanol, and 60 ml of water. The organic phase obtained was washed with 60 ml of water, and with a mixture of 20 ml of ethanol and 60 ml of water. The organic phase was washed with 60 ml of water, collected and dried. Distilling away the solvent resulted in 1.6 g of L-carnitine 2-butyloctanoate hydrochloride.

The structure of the compound obtained was identified by NMR, liquid chromatography-mass spectroscopy (LC/MS) and elemental analysis as described in Synthetic Example 1.

<NMR>
$^1$H-NMR (CDCl$_3$): 2.76 ppm (1H, d, 6.0 Hz), 2.80 ppm (1H, m), 3.76 ppm (1H, d, 14.4 Hz), 3.94 ppm (1H, dd, 14.4, 8.2 Hz), 5.60-5.64 ppm (1H, m)

<Liquid Chromatography-Mass Spectroscopy (LC/MS)>
MS (ESI) m/z: 344.5 [M$^+$]

<Elemental Analysis>
C, 60.1%, H, 9.5%, N, 3.5%, O, 16.7%, Cl, 10.2%.

Example 1

Percutaneous Absorption Properties

The following five substances were tested:
1) L-carnitine hydrochloride (Sigma-Aldrich)
2) L-carnitine palmitate hydrochloride (Sigma-Aldrich)
3) L-carnitine 2-hexyldecanoate hydrochloride (Synthetic Example 1)
4) L-carnitine 2-methylpalmitate hydrochloride (Synthetic Example 2)
5) L-carnitine 2-butyloctanoate hydrochloride (Synthetic Example 3)

The test substances (1) and (2) were standard references.

The test substances were each dissolved in Dulbecco's PBS (−) containing 5% by mass of 1,2-hexanediol, followed by adding 1N NaOH to adjust the pH to 7. Consequently, 0.3% by mass solutions of the test substances were prepared. Two chambers were separated through a three-dimensional model of human skin tissue (TESTSKIN™ LSD-d, available from TOYOBO CO., LTD.). 3 ml of each test substance solution was placed into a chamber on the epidermis side, and 3 ml of Dulbecco's PBS (−) was placed into a chamber on the dermis side. They were stirred with magnetic stirrers at 35° C. for 24 hours.

After the lapse of 24 hours, 1 ml of the buffer solution in the dermis-side chamber was collected, and 0.5 ml of the solution collected was analyzed to determine free carnitine. The remaining portion of the solution collected was adjusted to pH 11 with 1N NaOH, was encapsulated in a 1.5 ml screw vial, and was allowed to stand at 80° C. for 6 hours, followed by cooling. The pH of the solution was adjusted to 7 with 1N HCl, whereby all acylcarnitine derivatives were decomposed to free carnitine. These solutions were each combined with 0.02 ml of 1N hydrochloric acid, 0.1 ml of 1.6% by mass 1-aminoanthracene-in acetone solution and 0.1 ml of 16% by mass aqueous EDC (1-ethyl-3-(3-dimethylaminopropyl)carbodiimide hydrochloride) solution, followed by sufficient stirring. The solutions were allowed to stand still at room temperature for 20 minutes and were washed with 3 ml of diethylether. The aqueous phases were filtered and were analyzed by reversed-phase high performance liquid chromatography (RPHPLC) (column: Phenomenex Synergi-RP, eluting solution: 45% acetonitrile, flow rate: 1.0 ml/min) to determine peak intensities assigned to 1-aminoanthracene-modified carnitine (excitation wavelength: 248 nm, fluorescent wavelength: 418 nm). The concentrations of carnitine derivatives and free carnitine originating from the test substances in the solution in the dermis-side chamber were calculated and determined from the aforesaid peak intensities. The alkali and heat treated sample indicated the concentration of free carnitine and carnitine derivatives combined. The untreated sample indicated the concentration of free carnitine.

The results are given in FIG. 1.

FIG. 1 shows that L-carnitine 2-hexyldecanoate, L-carnitine 2-methylpalmitate and L-carnitine 2-butyloctanoate penetrated the skin and achieved comparable or higher L-carnitine concentrations than that obtained with L-carnitine palmitate.

Example 2

Stability

The following five substances were tested:
1) Acetyl L-carnitine hydrochloride (Sigma-Aldrich)
2) L-carnitine palmitate hydrochloride (Sigma-Aldrich)
3) L-carnitine 2-hexyldecanoate hydrochloride (Synthetic Example 1)
4) L-carnitine 2-methylpalmitate hydrochloride (Synthetic Example 2)
5) L-carnitine 2-butyloctanoate hydrochloride (Synthetic Example 3)

The test substances (1) and (2) were standard references.

The test substances were each dissolved in Dulbecco's PBS (−) containing 5% by mass of 1,2-hexanediol, followed by adding 1N NaOH to adjust the pH to 7. Consequently, 0.3% by mass solutions of the test substances were prepared. The solutions were tightly encapsulated in glass vials and were temperature controlled at 80° C. in a water bath.

Figure 2:
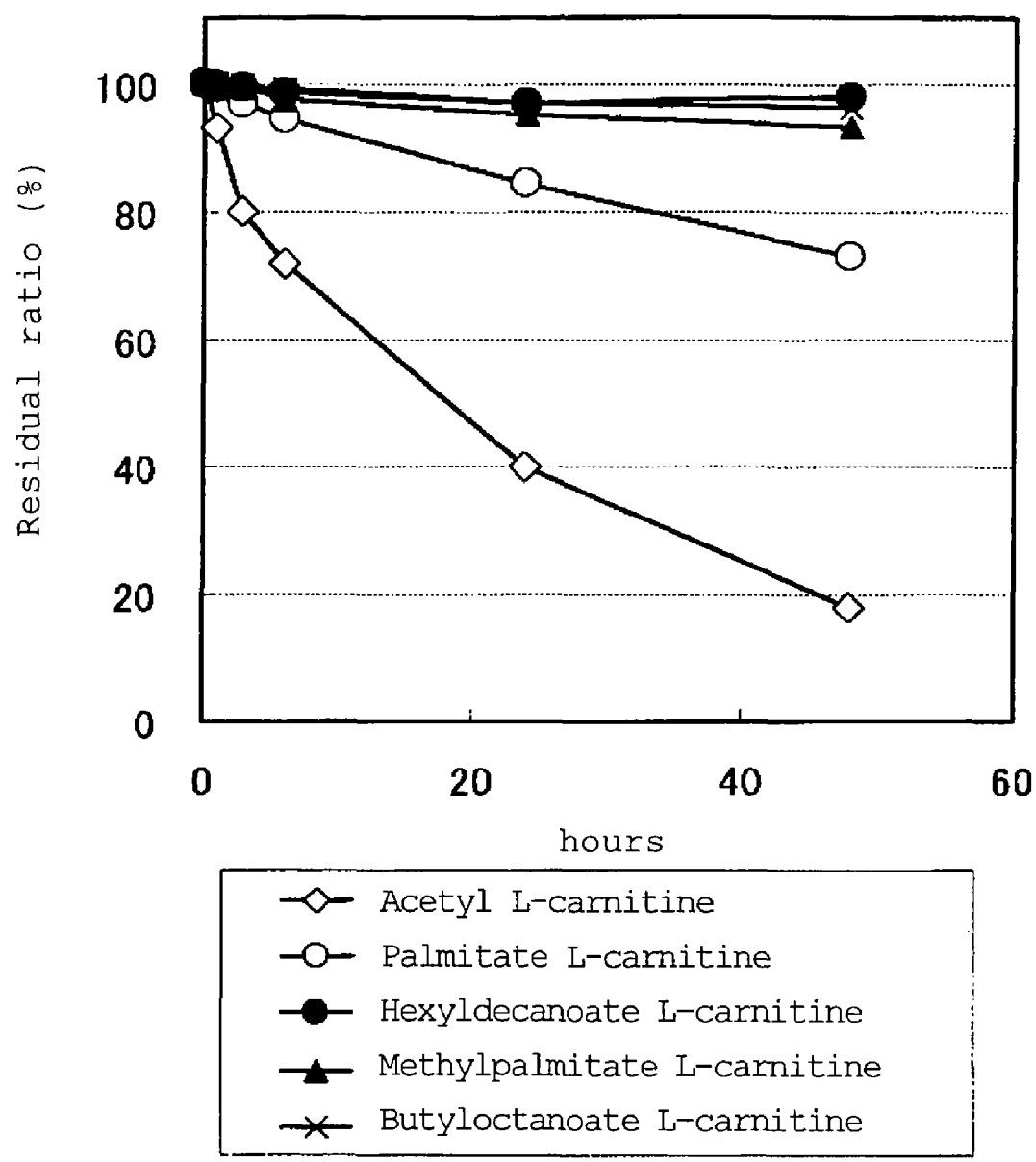
FIG. 2 is a graph showing changes with time of residual ratio of carnitine derivatives originating from the test substances in aqueous solutions in Example 2.

After the lapse of a predetermined time, the solutions were collected and were analyzed by RPHPLC (column: Shodex C8-5B, eluting solution: 70% acetonitrile, flow rate: 1.0 ml/min). The remaining carnitine derivatives originating from the test substances were determined from the UV absorption intensity at 210 nm. FIG. 2 shows changes with time of residual ratio of carnitine derivatives originating from the test substances.

FIG. 2 shows that the carnitine derivatives having a α-branched acyl group: L-carnitine 2-hexyldecanoate, L-carnitine 2-methylpalmitate and L-carnitine 2-butyloctanoate indicated higher residual ratio and were exceptionally more stable in aqueous solutions than the acylcarnitines having a straight-chain acyl group.

Example 3

Fat Breakdown Stimulation

Human preadipocytes (available from TOYOBO Co., LTD.) were seeded on a 96-well microplate and were incubated at 37° C. and 5% $CO_2$ using human preadipocyte growth medium TAGM (available from TOYOBO Co., LTD.) while renewing the medium every two days. The growth medium was changed to human adipocyte differentiation medium TADM (available from TOYOBO Co., LTD.), and incubation was carried out for 5 days. Subsequently, the medium was changed to an evaluation medium as shown in Table 1 below without or with 50 μM of any of the test substances described below. The incubation was carried out for 5 days.

The following five substances were tested:
1) L-carnitine hydrochloride (Sigma-Aldrich)
2) L-carnitine palmitate hydrochloride (Sigma-Aldrich)
3) L-carnitine 2-hexyldecanoate hydrochloride (Synthetic Example 1)
4) L-carnitine 2-methylpalmitate hydrochloride (Synthetic Example 2)
5) L-carnitine 2-butyloctanoate hydrochloride (Synthetic Example 3)

The test substances (1) and (2) were standard references.

TABLE 1

(Evaluation medium)

| Components | Concentration (g/l) |
| --- | --- |
| Calcium chloride dihydrate | 0.265 |
| Iron nitrate nonahydrate | 0.0001 |
| Magnesium sulfate | 0.09767 |
| Potassium chloride | 0.4 |
| Sodium carbonate | 3.7 |
| Sodium chloride | 6.4 |
| Sodium dihydrogen phosphate | 0.109 |
| L-arginine hydrochloride | 0.084 |
| L-cystine hydrochloride | 0.0626 |
| L-glutamine | 0.584 |
| Glycine | 0.030 |
| L-histidine hydrochloride hydrate | 0.042 |
| L-isoleucine | 0.105 |
| L-leucine | 0.105 |
| L-lysine hydrochloride | 0.146 |
| L-methionine | 0.030 |
| L-phenylalanine | 0.066 |
| L-serine | 0.042 |
| L-threonine | 0.095 |
| L-tryptophan | 0.016 |
| L-tyrosine disodium dihydrate | 0.10379 |
| L-valine | 0.094 |
| Choline hydrochloride | 0.004 |
| Folic acid | 0.004 |
| Myo-inositol | 0.0072 |
| Niacinamide | 0.004 |
| Calcium D-pantothenate | 0.004 |
| Pyridoxine hydrochloride | 0.004 |
| Riboflavin | 0.0004 |
| Thiamine hydrochloride | 0.004 |
| Phenol red sodium | 0.0159 |
| Sodium pyruvate | 0.11 |
| pH | 7.3 |

The adipocytes were washed with Dulbecco's PBS (−) three times and were formalin fixed. The adipocytes were stained with an oil red/water-isopropanol (1/1) solution, and were extracted with isopropanol. Triglyceride accumulated in the adipocytes was determined by a colorimetry method. Table 2 shows triglyceride accumulation obtained with the test substances relative to untreated adipocytes (100).

TABLE 2

| Test substances | Triglyceride accumulation |
| --- | --- |
| Not added | 100 |
| L-carnitine hydrochloride | 98 |
| L-carnitine palmitate hydrochloride | 87 |
| L-carnitine 2-hexyldecanoate hydrochloride | 89 |
| L-carnitine 2-methylpalmitate hydrochloride | 89 |
| L-carnitine 2-butyloctanoate hydrochloride | 90 |

Table 2 shows that, as acyl carnitines, L-carnitine 2-hexyldecanoate, L-carnitine 2-methylpalmitate and L-carnitine 2-butyloctanoate had good effects of stimulating fat metabolism.

Example 4

A cosmetic containing L-carnitine 2-hexyldecanoate hydrochloride was prepared according to Table 3. The cosmetic was stored at 40° C. for 3 months and proved to be stable without separation and precipitation.

TABLE 3

| Components | % |
| --- | --- |
| Sodium chloride | 0.2 |
| Tetrasodium EDTA | 0.2 |
| 1,2-Hexanediol | 4.0 |
| Dipotassium glycyrrhizinate | 0.1 |
| 1% aqueous sodium hyaluronate solution | 4.0 |
| L-carnitine 2-hexyldecanoate hydrochloride | 0.3 |
| Purified water | Balance |

Note:
The values are % by mass relative to the total 100%.

Example 5

Preparation of Skin Toners

Skin toners were manufactured according to Formulation Examples 1 to 4 below, in which the total of the components A and B was 100%.

Formulation Example 1

| A. | |
| --- | --- |
| Dipotassium glycyrrhizinate | 0.2% |
| L-carnitine 2-hexyldecanoate hydrochloride | 1.0% |
| Citric acid | 0.1% |
| Sodium citrate | 0.3% |
| Purified water | Balance |
| B. | |
| Polyoxyethylene sorbitol tetraoleate | 0.9% |
| Sorbitan monooleate | 0.1% |
| Olive oil | 0.1% |
| Dipropylene glycol | 5.0% |
| Methylparaben | 0.1% |
| Ethanol | 10.0% |

Formulation Example 2

| A. | |
| --- | --- |
| Sodium citrate | 0.1% |
| Glycerin | 8.0% |
| Sodium pyrrolidonecarboxylate | 1.0% |
| Trehalose | 0.03% |
| 1,3-Butylene glycol | 5.0% |
| Purified water | Balance |
| B. | |
| Polyoxyethylene polyoxypropylene decyltetradecyl ether | 0.6% |
| Methylparaben | 0.1% |
| Ethanol | 10.0% |
| L-carnitine 2-hexyldecanoate hydrochloride | 0.3% |

Formulation Example 3

| A. | |
|---|---|
| Polyvinyl alcohol | 0.1% |
| Carboxyvinyl polymer | 0.2% |
| Glycerin | 3.0% |
| Trisodium edetate | 0.1% |
| Sodium hydroxide | 0.05% |
| 2-Amino-2-methyl-1-propanol | 0.06% |
| Caffeine | 0.1% |
| Purified water | Balance |
| B. | |
| Ethanol | 20.0% |
| Polyoxyethylene oleyl ether | 0.3% |
| Methylparaben | 0.1% |
| Menthol | 0.1% |
| L-carnitine 2-methylpalmitate hydrochloride | 0.1% |

In Formulation Examples 1, 2 and 3, the ingredients of A and B were mixed together separately and were heated at 50° C. to give solutions. Subsequently, with A being stirred, small portions of B were added to A and were dissolved therein. The resultant solution was cooled with stirring. When the temperature was 30° C., the stirring was cancelled and the solution was allowed to stand to give a skin toner.

Formulation Example 4

| A. | |
|---|---|
| 1,3-Butylene glycol | 5.02% |
| Di(cholesteryl/behenyl/octyldodecyl) lauroyl glutamate | 0.5% |
| Trehalose | 0.03% |
| Trioctanoin | 0.03% |
| PEG-58 hydrogenated castor oil isostearate | 1.5% |
| PEG-60 hydrogenated castor oil | 0.5% |
| Methylparaben | 0.2% |
| Propylparaben | 0.01% |
| Tocopherol | 0.05% |
| L-carnitine 2-butyloctanoate hydrochloride | 0.3% |
| B. | |
| Sodium malate | 0.1% |
| Malic acid | Moderate amount |
| Purified water | Balance |

The ingredients of A and B were mixed together separately and were heated at 60° C. to give solutions. Subsequently, with A being stirred, B was admixed with A and the mixture was cooled to form a uniform skin toner.

Example 6

Preparation of Skin Milks

Skin milks were manufactured according to Formulation Examples 5 to 7. In Formulation Examples 5 and 6, the total of the components A and B was 100%. In Formulation Example 7, the total of the components A to C was 100%.

Formulation Example 5

| A. | |
|---|---|
| Squalane | 10.0% |
| Polyoxyethylene glyceryl isostearate | 3.5% |
| Polyoxyethylene hydrogenated castor oil triisostearate | 6.5% |
| Polyoxyethylene hydrogenated castor oil pyroglutamate isostearate | 12.0% |
| Methylparaben | 0.1% |
| B. | |
| L-carnitine 2-hexyldecanoate hydrochloride | 0.5% |
| Purified water | Balance |

The ingredients of A and B were mixed together separately, and A and B were heated at 70° C. and 50° C., respectively, to give solutions. Subsequently, with A being stirred, small portions of B were added to A to form an emulsion. The emulsion was cooled with stirring to obtain emulsified product, and the emulsified product was diluted ten times with purified water to yield a skin milk.

Formulation Example 6

| A. | |
|---|---|
| Liquid paraffin | 10.6% |
| Isopropyl myristate | 0.6% |
| Oleyl alcohol | 1.2% |
| Polyoxyethylene stearyl ether | 3.4% |
| PEG distearate | 1.9% |
| Polyoxyethylene polyoxypropylene tetradecyl ether | 0.4% |
| L-carnitine 2-hexyldecanoate hydrochloride | 0.3% |
| B. | |
| Sodium stearoylglutamate | 0.1% |
| Propylene glycol | 1.4% |
| Methylparaben | 0.1% |
| PEG-400 | 0.2% |
| Purified water | Balance |

The ingredients of A and B were mixed together separately, and A and B were heated at 70° C. and 75° C., respectively, to give solutions. Subsequently, with B being stirred, small portions of A were added to B to form an emulsion. The emulsion was cooled with stirring to yield a skin milk.

Formulation Example 7

| A. | |
|---|---|
| Polyoxyethylene sorbitan monostearate | 1.0% |
| Polyoxyethylene sorbitol tetraoleate | 0.5% |
| Sorbitan monostearate | 1.0% |
| Stearic acid | 0.5% |
| Behenyl alcohol | 0.5% |
| Beeswax | 0.5% |
| Squalane | 10.0% |
| Glyceryl tri-2-ethylhexanoate | 10.0% |
| Decaglyceryl decaoleate | 3.0% |
| 1,3-Butylene glycol | 7.0% |

-continued

| | |
|---|---|
| Methylparaben | 0.1% |
| L-carnitine 2-methylpalmitate hydrochloride | 0.3% |
| B. | |
| Xanthan gum | 0.04% |
| Carboxyvinyl polymer | 0.08% |
| Purified water | Balance |
| C. | |
| Triethanol amine | 0.05% |
| Purified water | 4.95% |

The ingredients of A, B and C were mixed together separately, and A and B were heated at 80° C. to give solutions whilst C was homogenized at room temperature. Subsequently, with A being stirred, B was added to A to form an emulsion, to which C was added. Cooling with stirring formed a milky liquid at near 40° C. The milky liquid composition was cooled to room temperature to yield a skin milk.

Example 7

Preparation of Gels

Gels were manufactured according to Formulation Examples 8 to 13. In Formulation Example 8, the total of the components A and B was 100%. In Formulation Example 9, the total of the components A to E was 100%. In Formulation Examples 10 to 13, the total of the components A to C was 100%.

Formulation Example 8

| | |
|---|---|
| A. | |
| Agar | 2.0% |
| Xanthan gum | 0.2% |
| Caffeine | 0.1% |
| Purified water | 50.0% |
| B. | |
| Glycerin | 7.0% |
| PEG-1500 | 8.0% |
| Methylparaben | 0.1% |
| L-carnitine 2-hexyldecanoate hydrochloride | 0.8% |
| Purified water | Balance |

The ingredients of A and B were mixed together separately, and A and B were heated at 90° C. and 50° C., respectively, to give dispersions. Subsequently, A was cooled to 50° C. With A being stirred, B was added to A and the mixture was gelled by cooling to not more than 30° C. with stirring. When the gel became sufficiently solid, it was crushed into a microgel with use of a dispersing device, followed by deaeration to produce a uniform (semitransparent) gel.

Formulation Example 9

| | |
|---|---|
| A. | |
| Carboxyvinyl polymer | 0.35% |
| Purified water | 50.0% |
| B. | |
| Sodium hydroxide | 0.1% |
| Purified water | 10.0% |
| C. | |
| 1% Aqueous sodium hyaluronate solution | 6.0% |
| Purified water | Balance |
| D. | |
| Polyoxyethylene polyoxypropylene tetradecyl ether | 0.3% |
| Ethanol | 5.0% |
| Methylparaben | 0.1% |
| L-carnitine 2-hexyldecanoate hydrochloride | 0.3% |
| E. | |
| Perfluoropolyether | 0.2% |

The ingredients of A, B, C and D were mixed together separately. A and B were allowed to form solutions at room temperature, and C and D were heated at 50° C. and 40° C., respectively, to give solutions. Subsequently, with A being stirred, B was added to A and the mixture was gelled. Thereafter, C, D and E were added to the gel and mixed together by stirring, followed by deaeration to produce a uniform (semitransparent) gel.

Formulation Example 10

| | |
|---|---|
| A. | |
| Carboxyvinyl polymer | 0.5% |
| Purified water | 40.0% |
| B. | |
| Potassium hydroxide | 0.1% |
| Purified water | 10.0% |
| C. | |
| Dipropylene glycol | 10.0% |
| Methylparaben | 0.1% |
| Dipotassium glycyrrhizinate | 0.05% |
| Hydrolyzed collagen | 0.05% |
| L-carnitine 2-methylpalmitate hydrochloride | 0.5% |
| Purified water | Balance |

The ingredients of A, B and C were mixed together separately. A and B were allowed to form solutions at room temperature, and C was heated at 50° C. to give a solution. Subsequently, with A being stirred, B was added to A and the mixture was gelled. Thereafter, C was added to the gel and mixed together by stirring, followed by deaeration to produce a uniform (semitransparent) gel.

Formulation Example 11

| A. | |
|---|---|
| Glycerin | 10.0% |
| 1,3-Butylene glycol | 6.0% |
| Dimethicone | 2.0% |
| PEG-60 hydrogenated castor oil | 0.6% |
| Laureth-2 | 0.1% |
| Laureth-21 | 0.1% |
| Methylparaben | 0.26% |
| Propylparaben | 0.1% |
| Ethylparaben | 0.1% |
| Phenoxyethanol | 0.1% |
| Tocopherol acetate | 0.1% |
| Chitosan succinamide | 0.01% |
| Yeast extract | 0.1% |
| Ethanol | 0.01% |
| Perfume | 0.01% |
| L-carnitine 2-hexyldecanoate hydrochloride | 0.3% |
| B. | |
| Carboxyvinyl polymer | 0.5% |
| Urea | 0.02% |
| Glucosamine hydrochloride | 0.01% |
| Disodium edetate | 0.01% |
| Purified water | 50.0% |
| C. | |
| Arginine | 0.63% |
| Purified water | Balance |

The ingredients of A, B and C were mixed together separately. A was heated at 60° C. to give a solution, and B and C were allowed to form solutions at room temperature. Subsequently, with A being stirred, B was added to A and the mixture was gelled. Thereafter, C was added to the gel and mixed together by stirring, followed by cooling to room temperature to produce a uniform (semitransparent) gel.

Formulation Example 12

| A. | |
|---|---|
| Glycerin | 50.0% |
| L-carnitine 2-hexyldecanoate hydrochloride | 0.5% |
| Tourmaline | 5.0% |
| Olive oil | 1.0% |
| PEG-12 | 28.0% |
| PEG-75 | 7.5% |
| Polyglyceryl laurate | 1.0% |
| Ethanol | 0.49% |
| (Acrylic acid/alkyl (C10-30) acrylate) copolymer | 0.11% |
| Methylparaben | 0.11% |
| Propylparaben | 0.02% |
| Ginkgo extract | 0.02% |
| Tea extract | 0.02% |
| Horse chestnut extract | 0.02% |
| Brown algae extract | 0.02% |
| B. | |
| Carboxyvinyl polymer | 0.07% |
| Purified water | 3.0% |
| C. | |
| Sodium hydroxide | 0.01% |
| Purified water | Balance |

The ingredients of A, B and C were mixed together separately. A was heated at 60° C. to give a solution, and B and C were allowed to form solutions at room temperature. Subsequently, with A being stirred, B was added to A and the mixture was gelled. Thereafter, C was added to the gel and mixed together by stirring, followed by cooling to room temperature to produce a uniform (semitransparent) gel.

Formulation Example 13

| A. | |
|---|---|
| Decamethylcyclopentasiloxane | 20.0% |
| Potassium ascorbate | 3.0% |
| L-carnitine 2-butyloctanoate hydrochloride | 0.3% |
| B. | |
| Squalane | 50.0% |
| Light liquid isoparaffin | Balance |
| Dextrin palmitate | 8.0% |
| C. | |
| Octyl paramethoxycinnamate | 1.0% |
| Phenoxyethanol | 0.5% |
| α-tocopherol | 0.1% |

The ingredients of A, B and C were separately weighed out. The ingredients of A were kneaded at room temperature with a bead mill. The ingredients of B were heated to give a uniform solution. The ingredients of C were allowed to form a solution at room temperature. Subsequently, with B being stirred, C was added to B. The mixture was homogenized and was cooled to room temperature with stirring. Thereafter, A was added and the mixture was stirred sufficiently to produce a uniform (semitransparent) gel.

Example 8

Preparation of Serums

Serums were manufactured according to Formulation Examples 14 to 16. In Formulation Example 14, the total of the components A to D was 100%. In Formulation Example 15, the total of the components A and B was 100%. In Formulation Example 16, the total of the components A to C was 100%.

Formulation Example 14

| A. | |
|---|---|
| Xanthan gum | 0.4% |
| Hydroxyethyl cellulose | 0.1% |
| Carboxyvinyl polymer | 0.1% |
| 1,3-Butylene glycol | 5.0% |
| L-carnitine 2-hexyldecanoate hydrochloride | 0.3% |
| Purified water | 50.0% |
| B. | |
| Potassium hydroxide (1% aqueous solution) | 2.5% |
| Purified water | 10.0% |
| C. | |
| Caffeine | 1.0% |
| Purified water | Balance |
| D. | |
| Methylparaben | 0.1% |
| Ethanol | 3.0% |

The ingredients of A, B, C and D were mixed together separately. A, B and D were allowed to form solutions at room temperature, and C was heated at 50° C. to give a solution. Subsequently, with A being stirred, B was added to A to form a viscous liquid. Thereafter, C and D were added thereto and mixed together by stirring to produce a uniform liquid (serum)

Formulation Example 15

| A. | |
|---|---|
| 1,3-Butylene glycol | 10.0% |
| Glycerin | 5.0% |
| Sodium hyaluronate | 0.2% |
| Xanthan gum | 0.2% |
| Dipotassium glycyrrhizinate | 0.02% |
| L-carnitine 2-methylpalmitate hydrochloride | 0.3% |
| Purified water | Balance |
| B. | |
| Ethanol | 3.0% |
| Hydrogenated lecithin | 0.5% |
| Trioctanoin | 0.3% |
| Diphenyl dimethicone | 0.2% |
| Methylparaben | 0.22% |
| Phenoxyethanol | 0.08% |
| PEG-50 hydrogenated castor oil | 0.1% |
| PEG-60 hydrogenated castor oil | 0.1% |
| α-tocopherol | 0.01% |
| Polyglyceryl-10 myristate | 0.05% |

The ingredients of A and B were mixed together separately, and A and B were heated at 50° C. to give solutions. Subsequently, with A being stirred, B was admixed with A with stirring, and the mixture was cooled with stirring to produce a uniform liquid (serum).

Formulation Example 16

| A. | |
|---|---|
| Xanthan gum | 0.4% |
| Hydroxyethyl cellulose | 0.4% |
| 1,3-Butylene glycol | 3.0% |
| Glycerin | 3.0% |
| Methylparaben | 0.1% |
| Purified water | Balance |
| B. | |
| L-carnitine 2-butyloctanoate hydrochloride | 0.3% |
| 1,2-Hexanediol | 4.0% |
| Purified water | 50.0% |
| C. | |
| Magnesium ascorbic acid-2-phosphate | 1.5% |
| Sodium ascorbic acid-2-phosphate | 1.5% |
| Sodium citrate | 0.5% |
| Tetrasodium edetate | 0.1% |
| Purified water | 9.4% |

The ingredients of A, B and C were mixed together separately. A and C were allowed to form solutions at room temperature, and B was heated at 50° C. to give a solution. Subsequently, with A being stirred, B was added to A to form a viscous liquid. Thereafter, C was admixed with stirring to produce a uniform liquid (serum).

Example 9

Preparation of Creams

Creams were manufactured according to Formulation Examples 17 to 19, in which the total of the components A and B was 100%.

Formulation Example 17

| A. | |
|---|---|
| Hydrogenated rapeseed oil alcohol | 4.2% |
| Isononyl isononanoate | 6.0% |
| Squalane | 9.6% |
| Octyldoodecyl myristate | 4.8% |
| Polyglyceryl monostearate | 2.0% |
| Glyceryl stearate | 1.0% |
| Propylparaben | 0.05% |
| Xanthan gum | 0.1% |
| α-tocopherol | 0.5% |
| B. | |
| 1,3-Butylene glycol | 4.8% |
| Glycerin | 4.8% |
| L-carnitine 2-hexyldecanoate hydrochloride | 0.8% |
| Sodium ascorbic acid-2-phosphoric acid-6-palmitate | 1.0% |
| Methylparaben | 0.1% |
| Purified water | Balance |

The ingredients of A and B were mixed together separately, and A and B were heated at 85° C. to give solutions. Subsequently, with A being stirred, B was added to A to give an emulsion. The emulsion was cooled with stirring. When the temperature was approximately 40° C., the stirring was cancelled and the emulsion was deaerated to produce a cream.

Formulation Example 18

A cream was manufactured according to Formulation Example 17, except that L-carnitine 2-hexyldecanoate hydrochloride was replaced by L-carnitine 2-methylpalmitate hydrochloride.

Formulation Example 19

A cream was manufactured according to Formulation Example 17, except that L-carnitine 2-hexyldecanoate hydrochloride was replaced by L-carnitine 2-butyloctanoate hydrochloride.

Example 10

Preparation of Sheet-Like Cosmetic Packs

Sheet-like cosmetic packs were manufactured according to Formulation Examples 20 to 23, in which the total of the components A and B was 100%.

Formulation Example 20

| | |
|---|---|
| A. Glycerin | 30.0% |
| Alumina magnesium hydroxide | 1.0% |
| B. Diisopropanolamine | 1.0% |
| Sodium polyacrylate | 2.0% |
| Acrylic acid/sodium acrylate copolymer (50/50 molar ratio) | 2.0% |
| L-carnitine 2-hexyldecanoate hydrochloride | 0.3% |
| Magnesium ascorbic acid-2-phosphate | 3.0% |
| Purified water | Balance |

Formulation Example 21

| | |
|---|---|
| A. 1,3-Butylene glycol | 30.0% |
| Aluminum hydroxide gel/sodium hydrogencarbonate coprecipitate | 0.05% |
| B. Sodium acrylate/acrylic acid copolymer (70/30 molar ratio) | 1.0% |
| Polyacrylic acid | 1.0% |
| N-vinylacetamide/sodium acrylate copolymer (9/1 weight ratio) | 3.0% |
| Aluminum lactate | 0.05% |
| 10% Aqueous ammonia solution | 0.01% |
| L-carnitine 2-hexyldecanoate hydrochloride | 2.0% |
| Magnesium ascorbic acid-2-phosphate | 0.01% |
| Purified water | Balance |

In Formulation Examples above, the ingredients of A and B were mixed together separately. A was allowed to form a dispersion at room temperature and B was heated at 50° C. to give a solution. Subsequently, B was cooled to room temperature with stirring, and A was gradually added to B with kneading. The resultant sol was applied on a polypropylene liner with a knife coater with clearances of 0.5 mm. Thereafter, a nonwoven fabric was attached onto the sol and these were placed in an aluminum laminated bag, which was then heat sealed. After three days of aging, a sheet-like cosmetic pack was obtained.

Formulation Example 22

A sheet-like cosmetic pack was manufactured according to Formulation Example 20, except that L-carnitine 2-hexyldecanoate hydrochloride was replaced by L-carnitine 2-methylpalmitate hydrochloride.

Formulation Example 23

A sheet-like cosmetic pack was manufactured according to Formulation Example 20, except that L-carnitine 2-hexyldecanoate hydrochloride was replaced by L-carnitine 2-butyloctanoate hydrochloride.

Example 11

Preparation of Packs

Packs (peel-off packs) were manufactured according to Formulation Examples 24 to 26, in which the total of the components A and B was 100%.

Formulation Example 24

| A. | |
|---|---|
| Polyvinyl alcohol | 13.0% |
| Carrageenan | 0.5% |
| Purified water | Balance |
| B. | |
| 1,3-Butylene glycol | 3.0% |
| Methylparaben | 0.1% |
| Ethanol | 8.0% |
| L-carnitine 2-hexyldecanoate hydrochloride | 1.0% |

The ingredients of A and B were mixed together separately. A was caused to swell by heating at 50° C. and B was allowed to form a solution at room temperature. Subsequently, with A being stirred, B was gradually added to A and mixed together. The mixture was cooled with stirring. When the temperature was approximately 30° C., the stirring was cancelled and the mixture was allowed to stand to produce a peel-off pack.

Formulation Example 25

A peel-off pack was manufactured according to Formulation Example 24, except that L-carnitine 2-hexyldecanoate hydrochloride was replaced by L-carnitine 2-methylpalmitate hydrochloride.

Formulation Example 26

A peel-off pack was manufactured according to Formulation Example 24, except that L-carnitine 2-hexyldecanoate hydrochloride was replaced by L-carnitine 2-butyloctanoate hydrochloride.

Example 12

Preparation of Bath Agents

Bath agents were manufactured according to Formulation Examples 27 and 28, in which the total of the ingredients was 100%.

Formulation Example 27

| | |
|---|---|
| Polyoxyethylene sorbitol tetraoleate | 14.0% |
| Polyoxyethylene oleyl ether | 3.0% |
| Sorbitan sesquioleate | 3.0% |
| Squalane | 10.0% |
| Jojoba oil | 20.0% |
| Avocado oil | 5.0% |
| Propylparaben | 0.1% |
| L-carnitine 2-hexyldecanoate hydrochloride | 1.0% |
| Liquid paraffin | Balance |

Formulation Example 28

| | |
|---|---|
| Sodium hydrogencarbonate | 35.5% |
| Citric acid | 37.1% |
| Polyethylene glycol | 2.1% |
| Magnesium oxide | 1.1% |
| α-tocopherol | 1.2% |
| Sodium ascorbic acid-2-phosphate | 1.5% |
| Ascorbic acid-2-glucoside | 1.5% |
| L-carnitine 2-methylpalmitate hydrochloride | 0.5% |

In Formulation Examples above, the ingredients were stirred at room temperature to uniformity to produce bath agents.

Example 13

Preparation of Facial Cleansing Agents

Facial cleansing agents were manufactured according to Formulation Examples 29 to 31. In Formulation Examples 29 and 30, the total of the components A to C was 100%. In Formulation Example 31, the total of the components A and B was 100%.

Formulation Example 29

| A. | |
|---|---|
| Myristic acid | 15.0% |
| Palmitic acid | 5.0% |
| Stearic acid | 3.0% |
| Beeswax | 3.0% |
| PEG-6000 | 2.0% |
| Ethylene glycol distearate | 2.0% |
| Coconut fatty acid diethanolamide | 3.0% |
| Concentrated glycerin | 15.0% |
| L-carnitine 2-hexyldecanoate hydrochloride | 0.5% |
| B. | |
| Potassium hydroxide | 5.5% |
| Purified water | 14.5% |
| C. | |
| N-lauroylsarcosine sodium | 10.0% |
| Purified water | Balance |

The ingredients of A, B and C were mixed together separately. A and B were heated at 80° C. to give solutions, and C was allowed to form a solution at room temperature. Subsequently, with A being stirred, B was gradually added to A and thereafter C was added. The mixture was cooled with stirring. When the temperature was approximately 30° C., the stirring was cancelled and the solution was allowed to stand. Consequently, a facial cleansing agent was obtained.

Formulation Example 30

A facial cleansing agent was manufactured according to Formulation Example 29, except that L-carnitine 2-hexyldecanoate hydrochloride was replaced by L-carnitine 2-methylpalmitate hydrochloride.

Formulation Example 31

| A. | |
|---|---|
| Lauric acid | 2.0% |
| Myristic acid | 17.0% |
| Palmitic acid | 4.0% |
| Stearic acid | 4.0% |
| Potassium coconut fatty acid | 8.0% |
| Coconut fatty acid diethanolamide | 3.0% |
| N-cocoylmethyltaurine sodium | 10.0% |
| Concentrated glycerin | 10.0% |
| 1,3-Butylene glycol | 10.0% |
| L-carnitine 2-butyloctanoate hydrochloride | 1.0% |
| Potassium hydroxide | 5.5% |
| Tetrasodium edetate | 0.2% |
| Purified water | Balance |

B.

The ingredients of A and B were mixed together separately. A was heated at 80° C. to give a solution, and B was allowed to form a solution at room temperature. Subsequently, with A being stirred, B was gradually added to A. The mixture was cooled with stirring. When the temperature was approximately 30° C., the stirring was cancelled and the solution was allowed to stand. Consequently, a facial cleansing agent was obtained.

Example 14

Preparation of Shampoos

Shampoos were manufactured according to Formulation Examples 32 to 34, in which the total of the components was 100%.

Formulation Example 32

| | |
|---|---|
| Sodium POE (2) lauryl ether sulfate | 30.0% |
| Ammonium POE (2) lauryl ether sulfate | 20.0% |
| Betaine lauryldimethylaminoacetate | 6.0% |
| O-[2-hydroxy-3 (trimethylammonio)propyl]hydroxyethylcellulose chloride | 0.25% |
| Coconut fatty acid diethanolamide | 4.0% |
| Ethylene glycol distearate | 2.0% |
| 1,3-Butylene glycol | 3.0% |
| Disodium edetate | 0.2% |
| L-carnitine 2-hexyldecanoate hydrochloride | 1.0% |
| Purified water | Balance |

The ingredients were mixed together and were heated at 80° C. followed by stirring to give an emulsion. The emulsion was cooled with stirring. When the temperature was approximately 30° C., the stirring was cancelled and the emulsion was allowed to stand. Consequently, a shampoo was obtained.

Formulation Example 33

A shampoo was manufactured according to Formulation Example 32, except that L-carnitine 2-hexyldecanoate hydrochloride was replaced by L-carnitine 2-methylpalmitate hydrochloride.

Formulation Example 34

A shampoo was manufactured according to Formulation Example 32, except that L-carnitine 2-hexyldecanoate hydrochloride was replaced by L-carnitine 2-butyloctanoate hydrochloride.

Example 15

Preparation of Hair Tonics

Hair tonics were manufactured according to Formulation Examples 35 to 37, in which the total of the ingredients was 100%.

Formulation Example 35

| | |
|---|---|
| Salicylic acid | 0.3% |
| Menthol | 0.2% |
| Ethanol | 60.0% |
| Glycerin | 5.0% |
| L-carnitine 2-hexyldecanoate hydrochloride | 1.0% |
| Purified water | Balance |

The ingredients were mixed together and were allowed to give a solution at room temperature. Consequently, a hair tonic was obtained.

Formulation Example 36

A hair tonic was manufactured according to Formulation Example 35, except that L-carnitine 2-hexyldecanoate hydrochloride was replaced by L-carnitine 2-methylpalmitate hydrochloride.

Formulation Example 37

A hair tonic was manufactured according to Formulation Example 35, except that L-carnitine 2-hexyldecanoate hydrochloride was replaced by L-carnitine 2-butyloctanoate hydrochloride.

The invention claimed is:

1. An external skin preparation comprising a carnitine derivative represented by Formula (1) and/or a salt of carnitine derivative represented by Formula (2):

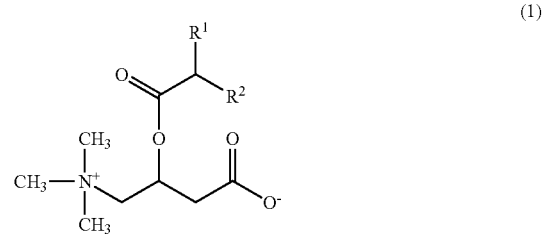

wherein one of $R^1$ and $R^2$ is a saturated aliphatic hydrocarbon group of 2 to 16 carbon atoms that may have a branch, and the other is a saturated aliphatic hydrocarbon group of 8 to 16 carbon atoms that may have a branch;

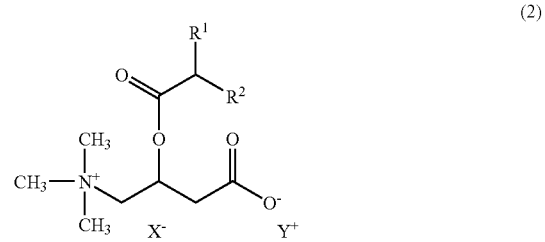

wherein $R^1$ and $R^2$ are as defined in Formula (1), $X^-$ is an inorganic or organic anion that maintains electrical neutrality with a cation part of the carnitine derivative, and $Y^+$ is an inorganic or organic cation that maintains electrical neutrality with an anion part of the carnitine derivative.

2. The external skin preparation according to claim 1, wherein one of $R^1$ and $R^2$ in Formulae (1) and (2) is a linear alkyl group of 6 carbon atoms, and the other is a linear alkyl group of 8 carbon atoms.

3. The external skin preparation according to claim 1, wherein $X^-$ in Formula (2) is an anion selected from the group consisting of hydroxide ion, nitrate ion, sulfate ion, carbonate ion, hydrogen carbonate ion, halide ion, formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion.

4. The external skin preparation according to claim 1, wherein $Y^+$ in Formula (2) is a cation selected from the group consisting of hydrogen ion, sodium ion, potassium ion, calcium ion, magnesium ion, zinc ion, ammonium ion, carnitine cation and carnitine derivative cation.

5. The external skin preparation according to claim 1, wherein the carnitine derivative represented by Formula (1) and/or the salt of carnitine derivative represented by Formula (2) accounts for 0.01 to 20% by mass of the external skin preparation.

6. A cosmetic comprising 0.01 to 20% by mass of the carnitine derivative and/or the salt of carnitine derivative described in claim 1.

7. The cosmetic according to claim 6, which is a cosmetic for stimulating lipid metabolism.

8. A carnitine derivative represented by Formula (3):

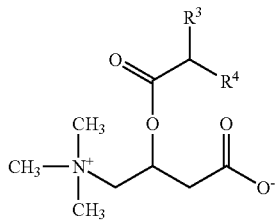

(3)

wherein one of $R^3$ and $R^4$ is a saturated aliphatic hydrocarbon group of 1 to 16 carbon atoms that may have a branch, and the other is a saturated aliphatic hydrocarbon group of 8 to 16 carbon atoms that may have a branch.

9. A salt of carnitine derivative represented by Formula (4):

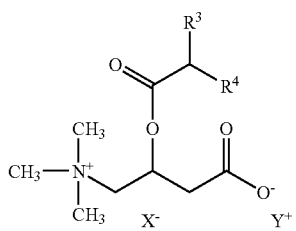

(4)

wherein one of $R^3$ and $R^4$ is a saturated aliphatic hydrocarbon group of 1 to 16 carbon atoms that may have a branch, the other is a saturated aliphatic hydrocarbon group of 8 to 16 carbon atoms that may have a branch, $X^-$ is an inorganic or organic anion that maintains electrical neutrality with a cation part of the carnitine derivative, and $Y^+$ is an inorganic or organic cation that maintains electrical neutrality with an anion part of the carnitine derivative.

10. A carnitine derivative represented by Formula (7):

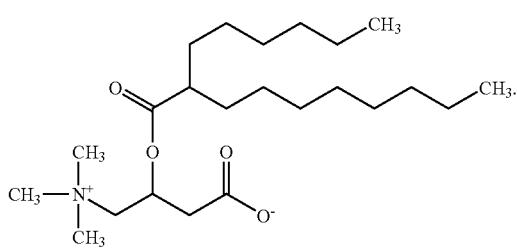

(7)

11. A salt of carnitine derivative represented by Formula (8):

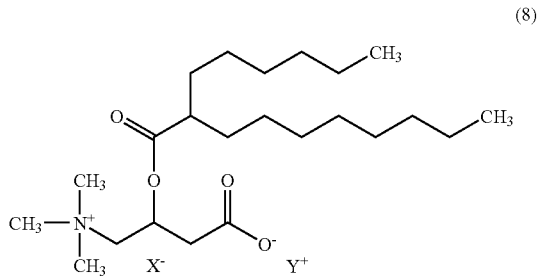

(8)

wherein $X^-$ is an inorganic or organic anion that maintains electrical neutrality with a cation part of the carnitine derivative, and $Y^+$ is an inorganic or organic cation that maintains electrical neutrality with an anion part of the carnitine derivative.

12. The salt of carnitine derivative according to claim 11, wherein $X^-$ in Formula (8) is an anion selected from the group consisting of hydroxide ion, nitrate ion, sulfate ion, carbonate ion, hydrogen carbonate ion, halide ion, formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion.

13. The salt of carnitine derivative according to claim 11, wherein $Y^+$ in Formula (8) is a cation selected from the group consisting of hydrogen ion, sodium ion, potassium ion, calcium ion, magnesium ion, zinc ion, ammonium ion, carnitine cation and carnitine derivative cation.

14. A carnitine derivative represented by Formula (9):

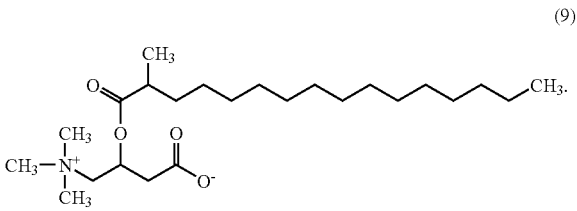

(9)

15. A salt of carnitine derivative represented by Formula (10):

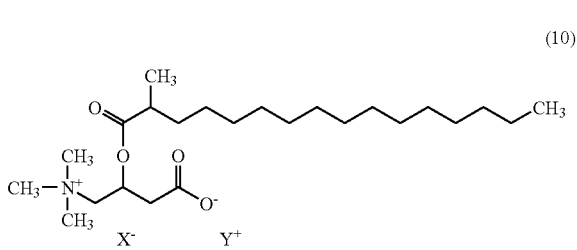

(10)

wherein X⁻ is an inorganic or organic anion that maintains electrical neutrality with a cation part of the carnitine derivative, and Y⁺ is an inorganic or organic cation that maintains electrical neutrality with an anion part of the carnitine derivative.

16. The salt of carnitine derivative according to claim 15, wherein X⁻ in Formula (10) is an anion selected from the group consisting of hydroxide ion, nitrate ion, sulfate ion, carbonate ion, hydrogen carbonate ion, halide ion, formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion.

17. The salt of carnitine derivative according to claim 15, wherein Y⁺ in Formula (10) is a cation selected from the group consisting of hydrogen ion, sodium ion, potassium ion, calcium ion, magnesium ion, zinc ion, ammonium ion, carnitine cation and carnitine derivative cation.

18. A carnitine derivative represented by Formula (11):

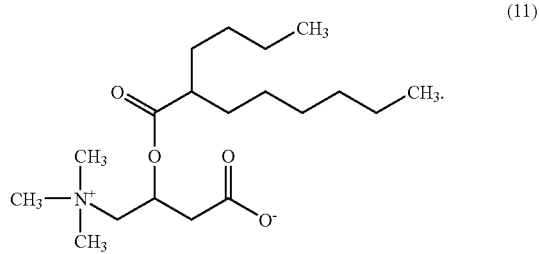

(11)

19. A salt of carnitine derivative represented by Formula (12):

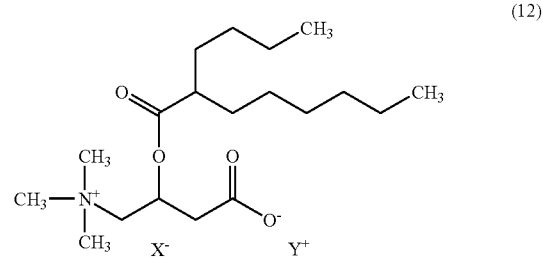

(12)

wherein X⁻ is an inorganic or organic anion that maintains electrical neutrality with a cation part of the carnitine derivative, and Y⁺ is an inorganic or organic cation that maintains electrical neutrality with an anion part of the carnitine derivative.

20. The salt of carnitine derivative according to claim 19, wherein X⁻ in Formula (12) is an anion selected from the group consisting of hydroxide ion, nitrate ion, sulfate ion, carbonate ion, hydrogen carbonate ion, halide ion, formate ion, acetate ion, citrate ion, tartrate ion, oxalate ion, fumarate ion, saturated or unsaturated fatty acid anion of 3 to 20 carbon atoms that may have a branch, carnitine anion, carnitine derivative anion, ascorbate anion, ascorbylphosphate anion and ascorbylphosphate derivative anion.

21. The salt of carnitine derivative according to claim 19, wherein Y⁺ in Formula (12) is a cation selected from the group consisting of hydrogen ion, sodium ion, potassium ion, calcium ion, magnesium ion, zinc ion, ammonium ion, carnitine cation and carnitine derivative cation.

* * * * *